United States Patent [19]

Matsumoto et al.

[11] Patent Number: 5,603,926

[45] Date of Patent: Feb. 18, 1997

[54] COSMETIC COMPOSITION COMPRISING CATIONIC POLYMER THICKENER

[75] Inventors: Junichi Matsumoto, Kashiwara; Yujiro Uchiyama, Osaka; Tetsuya Kambe; Tomiyuki Nanba, both of Yokohama; Yoshihiro Okuda, Higashiosaka, all of Japan

[73] Assignees: Osaka Yuki Kagaku Kogyo Kabushiki Kaisha, Osaka; Shiseido Company, Limited, Tokyo, both of Japan

[21] Appl. No.: 354,833

[22] Filed: Dec. 8, 1994

Related U.S. Application Data

[63] Continuation-in-part of Ser. No. 158,284, Nov. 29, 1993, abandoned.

[30] Foreign Application Priority Data

Dec. 1, 1992 [JP] Japan ................................. 4-321872

[51] Int. Cl.$^6$ ................................................. A61K 7/075
[52] U.S. Cl. ................................. 424/70.15; 424/70.122
[58] Field of Search ....................... 424/70.11, 78.18, 424/70.15, 70.18; 520/210, 264

[56] References Cited

U.S. PATENT DOCUMENTS

| | | | |
|---|---|---|---|
| 4,521,404 | 6/1985 | Lorenz et al. | 424/71 |
| 4,524,175 | 9/1985 | Fink et al. | 524/516 |
| 5,126,124 | 6/1992 | Tazi et al. | 424/47 |
| 5,208,014 | 5/1993 | Dubief et al. | 424/71 |
| 5,252,324 | 10/1993 | Bires et al. | 424/70.17 |
| 5,296,218 | 3/1994 | Chen et al. | 424/71 |
| 5,321,110 | 6/1994 | Shih | 526/264 |

FOREIGN PATENT DOCUMENTS

| | | |
|---|---|---|
| 0055801 | 7/1982 | European Pat. Off. |
| 0201342 | 12/1986 | European Pat. Off. |
| 5-721210 | 12/1982 | Japan |
| 4-106114 | 4/1992 | Japan |
| 4-108715 | 4/1992 | Japan |

OTHER PUBLICATIONS

European Search Report for EP 94103241.9.

*Primary Examiner*—Peter F. Kulkosky
*Attorney, Agent, or Firm*—Varndell Legal Group

[57] ABSTRACT

Cosmetic composition comprising cationic thickener prepared in a nonaqueous system in the absence of a surface active agent by polymerizing monomer composition containing 15 to 90% by weight of at least one of acrylic monomer having amino group and methacrylic monomer having amino group, 0 to 80% by weight of vinyl monomer, 1 to 60% by weight of monomer having at least one of acryloyl group and methacryloyl group and 0.1 to 25% by weight of crosslinkable vinyl monomer. This cosmetic composition imparts refreshing feeling and little skin irritation and can be suitably used as hair cream, hair lotion and the like.

3 Claims, 2 Drawing Sheets

COSMETIC COMPOSITION COMPRISING CATIONIC POLYMER THICKENER

CROSS-REFERENCE TO RELATED APPLICATION

This is a continuation-in-part of application Ser. No. 158,284 filed on Nov. 29, 1993, now abandoned.

BACKGROUND OF THE INVENTION

The present invention relates to a cosmetic composition containing a cationic thickener, and more particularly to a cosmetic composition which can be suitably used as, for instance, hair-conditioner, hair-setting cosmetics, hair dressing cosmetics, various cosmetic cream and the like.

As a thickener for a cosmetic composition, extracts of natural products such as quince seed gum have been conventionally used, but there is a possibility that these extracts are deteriorated by a hungas, a bacterium and the like. Therefore, a thickener made of a synthetic resin has been used in recent years.

As the typical thickener of the synthetic resin, there have been known a thickener made of a crosslinked polyacrylic acid prepared by crosslinking a polyacrylic acid with allyl saccharose and then adjusting its pH (Japanese Examined Patent Publication No. 4141/1957) and a thickener prepared by crosslinking a polyacrylic acid with an alkenyl ether and then adjusting its pH (Japanese Unexamined Patent Publication No. 46586/1976) have been known.

When these thickeners are used in cosmetics for hair, scalp and skin, a hard film is formed after drying, therefore excellent setting property is imparted to hair. However, there occurs some problems that hair cannot be easily combed and that a phenomenon that a film which is formed on hair is peeled off, that is, flaking is easily generated.

Also, when an anionic base gel made of the crosslinked polyacrylic acid is used, since this anionic base gel has —COOH groups in its molecule, and its main structure is an anionic polymer prepared by neutralizing all or a part of the —COOH groups with NaOH, KOH, an amine or the like, when raw materials for cosmetics for hair and scalp such as a cationic polymer for setting containing a quarternary amine are added thereto, neutralization of electric charge occurs between the anionic base gel and the raw materials and thereby coagulation, cloudiness, turbidity and the like are sometimes caused.

Accordingly, polymers for setting which can be added to the anionic base gel are only nonionic polymers such as polyvinylpyrrolidone and vinylpyrrolidone-vinyl acetate copolymer, and anionic polymers represented by an alkanolamine solution of an acrylic resin.

Also, it is not desirable that an acidic material such as lactic acid or succinic acid, which is admitted as an excellent pH adjusting agent for skin, is added as a raw material for cosmetics to an aqueous cosmetic composition containing the anionic base gel since lowering of viscosity or transparency of the cosmetic composition occurs. Therefore, the use of the aqueous cosmetic composition has been limited.

On the other hand, as a base gel which forms a soft and flexible film after drying, there is known a base gel which is prepared by carrying out an aqueous emulsion polymerization of a crosslinkable monomer and a monomer having an amino group and then adjusting a pH value to increase its viscosity (Japanese Unexamined Patent Publication No. 133145/1982). However, since the monomer is easily hydrolyzed, when the crosslinkable monomer is hydrolyzed and then neutralized by an acid treatment, a cationic group is introduced into the crosslinkable monomer. As a result, since an anionic group and a cationic group coexist in the same molecular chain of an obtained polymer, the polymer sometimes does not become uniform.

Also, when N,N-dimethylaminoethyl methacrylate is used as a raw material of the gel, a desirable polymer cannot be obtained since hydrolysis is caused with violence during the polymerization reaction in water. In other words, this fact means that there cannot be used N,N-dimethyl-aminoethyl methacrylate which is widely and industrially used and known as a raw material for cosmetics having excellent properties, and that there is inconvenience in the selection of the starting monomer for the cationic base gel. Also, there is a defect that the contamination with an impurity such as a surface active agent cannot be avoided.

Also, U.S. Pat. No. 4,542,175 discloses a method of thickening an aqueous system containing an aqueous dispersion of a polymer comprising (A) 20 to 100% by weight of a basic unsaturated free radically polymerizable monomer having at least one basic nitrogen atom, (B) 0 to 95% by weight of a neutral unsaturated free radically polymerizable comonomer and 0 to 30% by weight of a neutral unsaturated free radically polymerizable comonomer, which is prepared by aqueous emulsion polymerization. However, a dialkylaminoalkyl (meth)acrylate having a short alkyl group like a N,N-dimethylaminoethyl methacrylate cannot be used as one of the components for the polymer since the dialkylaminoalkyl (meth)acrylate is easily hydrolyzed during its polymerization reaction in water. Moreover, there are some defects such that impurities such as a surface active agent are contained in the resulting aqueous dispersion of the polymer, and that the polymer does not become uniform.

In order to solve the above problems, there is proposed a gel made of a copolymer prepared by copolymerizing a (meth)acrylic acid ester such as N,N-dimethylaminoethyl acrylate as disclosed in Japanese Unexamined Patent Publication No. 106114/1992, an oxyalkylene di(meth)acrylate and a vinyl monomer such as N-vinylpyrrolidone as disclosed in Japanese Unexamined Patent Publication No. 106114/1992. However, the gel is not good in flexibility and gloss of its formed film.

An object of the present invention is to provide a cosmetic composition comprising a cationic thickener, which can be preferably blended with not only a cationic polymer for setting but also the other polymer for setting which cannot be mixed with an anionic thickener.

Another object of the present invention is to provide a cosmetic composition comprising a cationic thickener which forms a flexible film after drying and contains little impurities.

A further object of the present invention is to provide a cosmetic composition which can be suitably used as hand cream, hair cream and the like.

A still further object of the present invention is to provide a cosmetic composition comprising a cationic thickener which is excellent in moisture resistance when the cosmetic composition is used together with a polymer for setting.

A still further object of the present invention is to provide a cosmetic composition which can be suitably used as a hair grooming preparation which shows excellent adhesive property to hair based upon the cationic polymer for setting.

These and other objects of the present invention will become apparent from the description hereinafter.

SUMMARY OF THE INVENTION

In accordance with the present invention, there is provided a cosmetic composition comprising a cationic thickener prepared in a nonaqueous system in the absence of a surface active agent by polymerizing a monomer composition containing (A) 15 to 90% by weight of at least one of an acrylic monomer having an amino group and a methacrylic monomer having an amino group represented by the general formula (I):

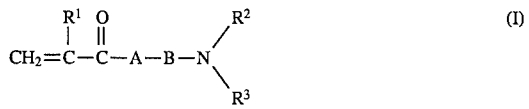

wherein $R^1$ is hydrogen atom or methyl group, each of $R^2$ and $R^3$ is independently hydrogen atom, methyl group, ethyl group or t-butyl group, A is oxygen atom or —NH— group, and B is a linear or branched alkylene group having 1 to 4 carbon atoms, (B) 0 to 80% by weight of a vinyl monomer represented by the general formula (II):

wherein $R^1$ is as defined above and $R^4$ is a group represented by the general formula:

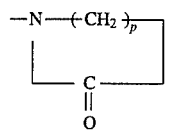

wherein p is 3 or 4, or a group represented by the formula:

(C) 1 to 60% by weight of at least one of a monomer having acryloyl group and a monomer having methacryloyl group represented by the general formula (III):

wherein $R^1$ and A are as defined above, $R^5$ is a linear or branched alkylene group having 8 to 20 carbon atoms or a group represented by the general formula (IV):

wherein n is an integer of 1 to 4, q is an integer of 1 to 25 and $R^6$ is hydrogen atom or methyl group, and (D) 0.1 to 25% by weight of a crosslinkable vinyl monomer.

DETAILED DESCRIPTION

Figure 1:
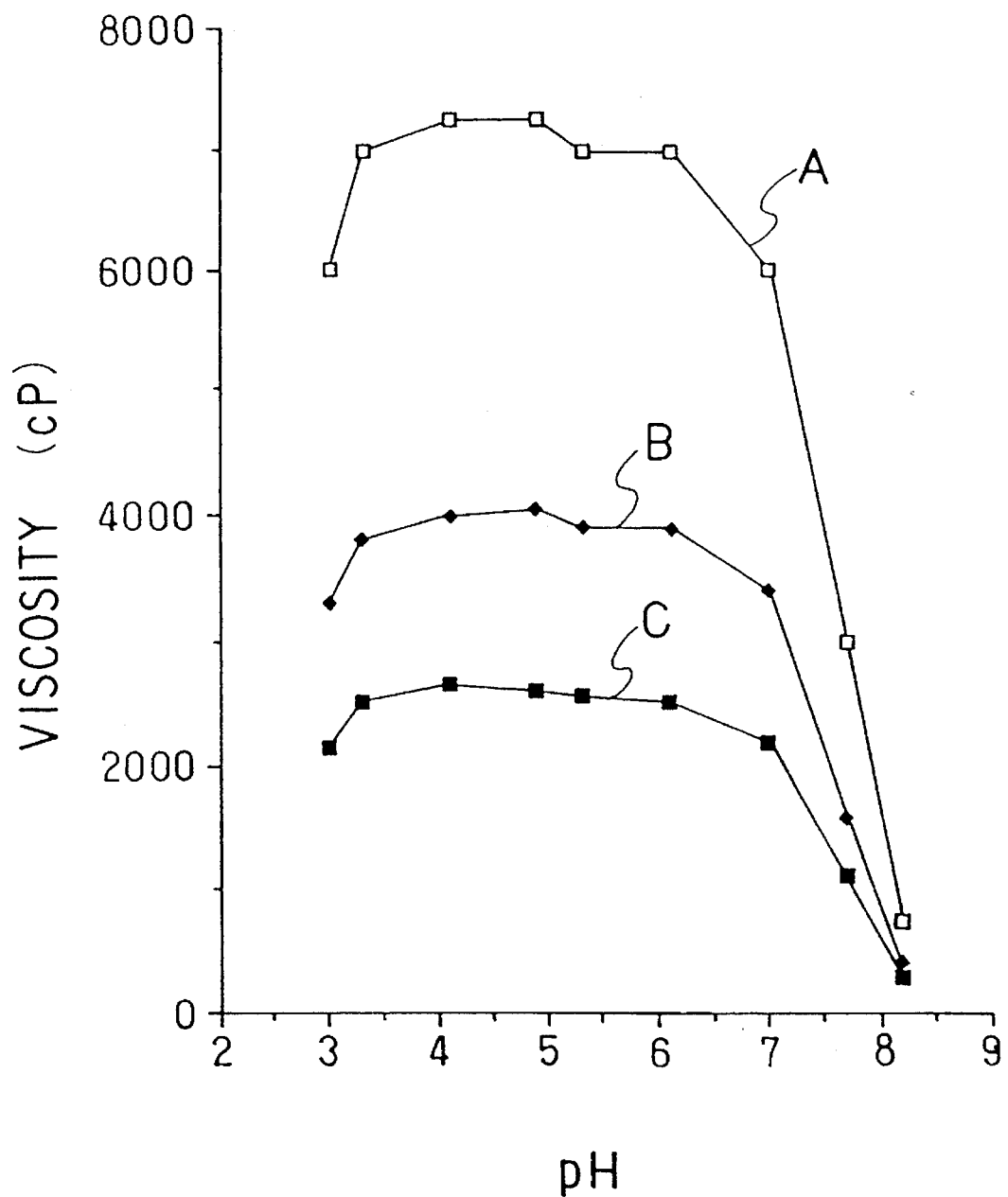
FIG. 1 is a graph showing a relation between pH and viscosity of 1% slurry solution of a polymer obtained in Experiment 1 according to the present invention.

As mentioned above, the cosmetic composition of the present invention comprises a cationic thickener prepared in a nonaqueous system in the absence of a surface active agent by polymerizing a monomer composition containing (A) 15 to 90% by weight of at least one of an acrylic monomer having an amino group and a methacrylic monomer having an amino group represented by the general formula (I):

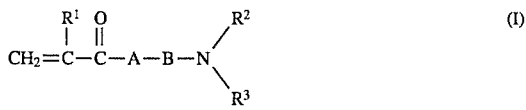

wherein $R^1$ is hydrogen atom or methyl group, each of $R^2$ and $R^3$ is independently hydrogen atom, methyl group, ethyl group or t-butyl group, A is oxygen atom or —NH— group, and B is a linear or branched alkylene group having 1 to 4 carbon atoms, (B) 0 to 80% by weight of a vinyl monomer represented by the general formula (II):

wherein $R^1$ is as defined above and $R^4$ is a group represented by the general formula:

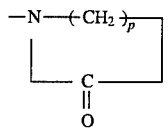

wherein p is 3 or 4, or a group represented by the formula:

(C) 1 to 60% by weight of at least one of a monomer having acryloyl group and a monomer having methacryloyl group represented by the general formula (III):

wherein $R^1$ and A are as defined above, $R^5$ is a linear or branched alkylene group having 8 to 20 carbon atoms, or a group represented by the general formula (IV):

wherein n is an integer of 1 to 4, and q is an integer of 1 to 25 and $R^6$ is hydrogen atom or methyl group, and (D) 0.1 to 25% by weight of a crosslinkable vinyl monomer.

The acrylic monomer having an amino group and the methacrylic monomer having an amino group [hereinafter referred to as "(meth)acrylic monomer having an amino group"] represented by the general formula (I) is used to impart properties based on cation to an obtained copolymer when the copolymer made of the monomer composition is neutralized with an adequate acid.

Typical examples of the (meth)acrylic monomer having an amino group are, for instance, N,N-dimethylaminoethyl acrylate, N,N-dimethylaminoethyl methacrylate, N,N-diethylaminoethyl acrylate, N,N-diethylaminoethyl methacrylate, N,N-dimethylaminopropyl acrylamide, N,N-dimethylaminopropyl methacrylamide and the like, and the present invention is not limited to the exemplified ones. In the present invention, these (meth)acrylic monomers having an amino group can be used alone or in an admixture thereof. Among them, N,N-dimethylaminoethyl (meth)acrylate can be particularly preferably used from the viewpoint of easier availability as an industrial raw material.

The content of the (meth)acrylic monomer having an amino group in the monomer composition is adjusted so as to become 15 to 90% by weight, preferably 25 to 85% by weight, more preferably 30 to 80% by weight. When the content of the (meth)acrylic monomer having an amino group is less than 15% by weight, the content of the (meth)acrylic monomer having an amino group to be neutralized later with an acid becomes too low and a cationic thickener having a sufficient gel viscosity cannot be easily obtained. When the content of the (meth)acrylic monomer having an amino group is more than 90% by weight, a film formed by drying the cosmetic composition comprising the cationic thickener loses its flexibility.

The vinyl monomer represented by the general formula (II) is used to impart flexibility, gloss and smoothness to a film formed from the cosmetic composition.

Typical examples of the vinyl monomer are, for instance, N-vinylpyrrolidone, N-vinylpiperidone, acrylamide, methacrylamide and the like, and the present invention is not limited to the exemplified ones. In the present invention, the vinyl monomer can be used alone or in an admixture thereof.

The content of the vinyl monomer in the monomer composition is adjusted so as to be at most 80% by weight, preferably at most 75% by weight, more preferably at most 60% by weight. When the content of the vinyl monomer is more than 80% by weight, the gel viscosity of an obtained cationic thickener is remarkably lowered. It is desired that the content of the vinyl monomer in the monomer composition is at least 3% by weight, preferably at least 5% by weight in order to sufficiently impart flexibility, gloss and smoothness to a film formed from the cosmetic composition.

The monomer having at least one of acryloyl group and the monomer having methacryloyl group [hereinafter referred to as "monomer having (meth)acryloyl group"] represented by the general formula (III) is used to improve gloss of a film formed from the cosmetic composition and increase a gel viscosity and compatibility with various polymers for setting.

In the general formula (III), it is desired that $R^5$ is a linear or branched alkylene group having 8 to 20 carbon atoms, preferably 10 to 20 carbon atoms and more preferably 13 to 18 carbon atoms in order to remarkably improve compatibility with cationic, nonionic and amphoteric polymers for setting, and to increase a gel viscosity.

Concrete examples of the monomer having (meth)acryloyl group are, for instance, lauryl acrylate, lauryl methacrylate, tridecyl acrylate, tridecyl methacrylate, stearyl acrylate, stearyl methacrylate, N-t-butylacrylamide, N-t-butylmethacrylamide, N-t-octylacrylamide, N-t-octylmethacrylamide, hydroxyethyl acrylate, hydroxyethyl methacrylate, hydroxypropyl acrylate, hydroxypropyl methacrylate, hydroxybutyl acrylate, hydroxybutyl methacrylate, polyoxyethylene acrylate or methacrylate represented by the general formula (IV) in which n is 2 and q is an integer of 2 to 9, methoxypolyethylene glycol acrylate or methacrylate represented by the general formula (IV) in which n is 3 and q is an integer of 2 to 23 and the like, and the present invention is not limited to the exemplified ones. In the present invention, the monomer having (meth)acryloyl group can be used alone or in an admixture thereof.

The content of the monomer having (meth)acryloyl group in the monomer composition is adjusted so as to be 1 to 60% by weight, preferably 1 to 55% by weight, more preferably 2 to 30% by weight. When the content of the monomer having (meth)acryloyl group is more than 60% by weight, the content of the hydrophobic groups contained in an obtained copolymer becomes high and water solubility is lowered even after the neutralization, and thereby a smooth gel cannot be easily obtained. When the content of the monomer having (meth)acryloyl group is less than 1% by weight, since the viscosity of a gel is lowered, there is a necessity to increase the amount of the cationic thickener and the usable amount of various resins for setting is lowered and at the same time the gloss of a film formed from the cosmetic composition is lowered.

The crosslinkable vinyl monomer is one of the essential components used in the monomer composition. If the crosslinkable vinyl monomer is not used in the monomer composition, an intended cationic thickener cannot be obtained.

The crosslinkable vinyl monomer has at least two carbon-carbon unsaturated double bonds in its molecule and is crosslinked with the other monomer.

Typical examples of the crosslinkable vinyl monomer are, for instance, acrylic monomers and methacrylic monomers having at least two carbon-carbon unsaturated double bonds in its molecule such as ethylene glycol diacrylate, ethylene glycol dimethacrylate, polyoxyethylene diacrylate, polyoxyethylene dimethacrylate, trimethylolpropane triacrylate, trimethylolpropane trimethacrylate, pentaerithritol triacrylate, pentaerithritol trimethacrylate, polypropylene glycol diacrylate such as tripropyleneglycol diacrylate and polypropylene glycol dimethacrylate; acrylamide monomers and methacrylamide monomers having at least two carbon-carbon unsaturated double bonds in its molecule such as methylenebisacrylamide, methylenebismethacrylamide, 1,2-bisacrylamidoethane, 1,2-bismethacrylamidoethane, 1,5-bisacrylamidopentane and 1,5-bismethacrylamidopentane; a vinyl monomer having at least two carbon-carbon unsaturated double bonds in its molecule such as divinylbenzene, and the like, and the present invention is not limited to the exemplified ones. In the present invention, the above-mentioned crosslinkable vinyl monomer can be used alone or in an admixture thereof.

The content of the crosslinkable vinyl monomer in the monomer composition is adjusted so as to be 0.1 to 25% by weight, preferably 1 to 20% by weight, more preferably 5 to 15% by weight. When the content of the crosslinkable vinyl monomer is less than 0.1% by weight, crosslinking density of an obtained cationic thickener becomes too low, and therefore, the viscosity of the cationic thickener cannot be heightened. When the content of the crosslinkable vinyl monomer is more than 20% by weight, the viscosity of the cationic thickener becomes high, but fine aggregates are generated in the gel and a uniform gel cannot be easily obtained.

The polymerization reaction of the monomer composition containing the (meth)acrylic monomer having an amino group, the vinyl monomer, the monomer having (meth)acryloyl group and the crosslinkable vinyl monomer is carried out in a nonaqueous system in the absence of a surface active agent by solution polymerization method, bulk polymerization method or extraction polymerization method which is usually employed when a powdery product is obtained. The extraction polymerization can be easily carried out in a nonaqueous system in the absence of a surface active agent by polymerizing the monomer composition using a mixture of a good solvent and a bad solvent to precipitate an obtained copolymer from the polymerization solution as explained below.

The polymerization is usually carried out in a nonaqueous system in the absence of a surface active agent while, for instance, heating the composition in a nonaqueous solvent under an atmosphere of inert gas such as nitrogen gas. The reason why the polymerization reaction is carried out in the nonaqueous system under an atmosphere of inert gas is that hydrolysis of ester groups existed in these monomers or an obtained copolymer is avoided. Also, the reason why a surface active agent is not used is that a uniform gel not containing impurities such as the surface active agent cannot be obtained.

Accordingly, when the monomer composition is polymerized with an aqueous emulsion method using a surface active agent, an intended cationic thickener cannot be obtained.

In the present invention, as the nonaqueous solvent, a good solvent solely, or a mixture of the good solvent and a bad solvent is used.

The good solvent is used in order to inhibit the generation of homopolymers caused by the difference of reactivity between each monomer and prepare a uniform copolymer.

In the present specification, the good solvent is intended to refer to a solvent which shows no turbid when at least 20 g of a copolymer having a molecular weight of at least 10,000 is dissolved in 100 ml of the solvent at 25° C.

Concrete examples of the good solvent are, for instance, methanol, ethanol, isopropanol, acetone, ethyl acetate, benzene, toluene, xylene and the like. Among these good solvents, ethanol, isopropanol and benzene are preferable since a copolymer having a relatively high molecular weight can be obtained.

Since an obtained cationic thickener is used in the cosmetic composition for human bodies, and benzene and the like are harmful to human bodies, ethanol and isopropanol are more preferable.

The bad solvent is used to easily precipitate an obtained copolymer from the polymerization solution.

The bad solvent is intended to refer to obtain a solvent in which a copolymer having a molecular weight of at least 10,000 is dissolved within the range of at most 5 g based upon 100 ml of the solvent at 25° C.

Concrete examples of the bad solvent are, for instance, linear, branched or cyclic aliphatic hydrocarbons having at most 15 carbon atoms such as n-pentane, n-hexane and cyclohexane, and the like. Among these bad solvents, linear, branched or cyclic aliphatic hydrocarbons having at most 7 carbon atoms and a relatively high boiling point are preferable. Among them, linear, branched or cyclic aliphatic hydrocarbons having 6 or 7 carbon atoms are particularly preferable since these hydrocarbons have a high boiling point. Also, n-hexane, cyclohexane and the like are preferable because these hydrocarbons are cheap and industrially excellent in handling.

It is preferable that the good solvent and the bad solvent are admixed together at a suitable ratio to obtain a cationic thickener without the deterioration of its properties.

When the ratio of the bad solvent is too high, there is a tendency that the polymerization rapidly proceeds, powder is precipitated in a short period of time and it becomes difficult to obtain a cationic thickener having desired physical properties. Therefore, it is desired that the content of the bad solvent in the mixture of the good solvent and the bad solvent is at most 98% by weight, preferably at most 97% by weight, and that the content of the good solvent in the mixture is at least 2% by weight, preferably at least 3% by weight.

It is preferable that a reactor is used for sufficiently stirring the monomer composition during the polymerization to efficiently give a cationic thickener. When a stirrer for solution polymerization which is generally used is used, it is preferable that the monomer composition for a thickener is diluted with the above solvent so that the concentration of the monomer composition becomes at most 30% by weight. Also, it is preferable that the monomer composition is sufficiently stirred with a stirrer or the like during the reaction in order to avoid the stagnation of reaction solution.

It is preferable that the polymerization reaction is carried out at a temperature of 50° to 100° C. The polymerization reaction is generally carried out at a reflux temperature of the solvent which is used in the reaction.

The period of time necessary for the polymerization reaction is generally at least 10 hours. The polymerization reaction can be voluntarily terminated when the amount of the remaining monomer becomes at most 10% by weight.

The amount of the remaining monomer can be determined by adding bromine to double bonds of the remaining monomer in accordance with a known method such as a PSDB method and measuring the amount of the double bonds.

Thus, a reaction solution containing a precipitate of the cationic thickener is obtained. The removal of the mixture of the good solvent and the bad solvent can be carried out, for instance, filtrating the obtained precipitate of the cationic thickener, conducting the precipitate to vacuum drying, or evaporating the solvent from the mixture under atmospheric pressure or reduced pressure.

During the polymerization reaction, a polymerization catalyst can be used. Examples of the polymerization catalyst are, for instance, azo compounds such as 2,2'-azobisisobutyronitrile, 2,2'-azobis(4-methoxy-2,4-dimethylvaleronitrile) and dimethyl-2,2'-azobisisobutylate, peroxides such as diacyl peroxides such as lauroyl peroxide; dialkyl peroxides such as di-t-butyl peroxide; peroxycarbonates such as diisopropyl peroxycarbonate; and peroxy esters such as t-butylperoxy pivalate and t-butylperoxy 2-ethylhexanoate. These polymerization catalysts can be used alone or in admixture thereof. Also, the present invention is not limited to the exemplified ones. When a lot of an amine monomer is used in the monomer composition, a side reaction is caused by a peroxide. Since there is a possibility that the polymerization is inhibited by the side reaction, it will be good to pay attention when using the peroxide. Therefore, generally, it is desired to mainly use the azo compounds. The kind of the polymerization catalyst is usually selected in accordance with the boiling point of the used solvent. For instance, when ethanol or benzene is used as the solvent, 2,2'-azobisisobutyronitrile is most prefereble from the viewpoint of the easiness of handling. It is desired that the amount of the polymerization catalyst is 0.05 to 3% by weight, preferably 0.1 to 1% by weight based upon the weight of the whole amount of the monomer composition.

During the polymerization of the monomer composition, various appearances are exhibited. For instance, when the good solvent is used solely, the same appearance as that shown in the conventional solution polymerization is exhibited in the early stages of the polymerization reaction. However, in the progress of the reaction, crosslinking reaction proceeds and a gelatinous appearance is shown. When the polymerization reaction further proceeds, a grease-like product having no precipitate is obtained.

When the mixture of the good solvent and the bad solvent is used, the same appearances as that shown by employing the general solution polymerization is exhibited in the early stages of the polymerization. However, in the progress of the polymerization reaction, the crosslinking reaction proceeds and the gelatinous appearance is shown. When the polymerization reaction further proceeds, the obtained polymer can be no longer dissolved in the mixture of the solvents, and is separated from the mixture in the form of precipitate.

Thus, a cationic thickener is obtained. The cationic thickener usually has a viscosity of 500 to 30000 cP, preferably 1500 to 15000 cP at 20° C. when the viscosity is measured by using a BH-type Brookfield viscometer commercially available from Tokyo Keiki Co., Ltd. (rotor No. 4) at 20 rpm after the cationic thickener is dispersed into water so that the concentration of the cationic thickener becomes 1% by weight, and the pH of the resulting aqueous cationic thickener is adjusted to 3.5 to 7 with lactic acid. Usually, after adjusting the pH value, the resulting aqueous cationic thickener is sufficiently stirred to obtain a clear and uniform aqueous cationic thickener.

The cationic thickener is used, for instance, by adding to various raw materials for cosmetics or by modifying into a gel.

The content of the cationic thickener contained in the cosmetic composition is voluntarily adjusted according to its desired uses. It is generally desired that the content of the cationic thickener is adjusted so as to become 0.01 to 30% by weight, preferably 0.1 to 10% by weight, more preferably 0.2 to 5% by weight.

When the cationic thickener is used as, for instance, a gel, generally, the content of the cationic thickener is preferably adjusted to 1 to 5% by weight and the viscosity of the gel is adjusted to be a desired viscosity.

When the cationic thickener is used as a gel, it is desired that the cationic thickener is neutralized by a suitable acidic material. When a gel containing water, an alcohol, a glycol or the like which is widely used in cosmeic compositions is prepared, it is desired that the cationic thickener is diluted with one or more selected from water, an alcohol, a glycol and the like to the concentration of at most 5% by weight and neutralized with a mineral acid such as sulfuric acid, hydrochloric acid or phosphoric acid or an organic acid such as acetic acid, citric acid, lactic acid, amino acid, succinic acid, malic acid, dimethyl sulfate or diethyl sulfate.

When an oily gel containing toluene, ethyl acetate or the like, which is used in a nail enamel remover, or squalane, liquid paraffin, liquid lanolin, octadodecyl myristate, octadodecyl oleate or the like, which is used as an oily raw material, is prepared, it is desired that the cationic thickener is diluted with at least one selected from the oily raw materials so that the content of the cationic thickener becomes at most 10% by weight and then the cationic thickener is neutralized with a lipophilic organic acid such as stearic acid, palmitic acid, myristic acid, lauric acid, 12-hydroxy-stearic acid or 2-ethylhexanoic acid as a neutralizer.

The viscosity of the thus obtained gel scarcely changes with the change of temperature. When the gel is mixed with water, an alcohol, glycerol, glycols, liquid paraffin, octadodecyl myristate, ethyl acetate or the like, which is widely used as a raw material for cosmetic compositions, the gel shows excellent thickening property and affinity to hydrophilic solvents and hydrophobic solvents.

The cosmetic composition of the present invention contains the cationic thickener. Also, besides the above-mentioned cationic thickener, adequate amount of various components for cosmetic compositions such as an excipient, a perfume, fats and oils, a surface active agent, a humectant, a pH adjusting agent, a thickener, an antiseptic, a silicone, an antioxidant, a UV-absorber, a pigment and the other thickeners which are generally used in cosmetic compositions can be added to the cosmetic composition of the present invention.

Concrete examples of the surface active agent are, for instance, anionic surface active agents such as a fatty acid soap, a higher alkyl sulfate, an alkyl ether sulfate, N-acyl sarcosinate, a higher fatty acid amide sulfonate, a phosphate, a sulfosuccinate, an alkylbenzenesulfonate, an N-acyl glutamate, a higher fatty acid ester sulfate, a polyoxyethylene [hereinafter reffered to as "POE"] alkyl ether carboxylate, a POE alkylaryl ether carboxylate, an α-olefin sulfonate, a higher fatty acid ester sulfonate, a secondary alcohol sulfate and a sulfate of higher fatty acid alkylolamide; cationic surfate active agents such as an alkyltrimethylammonium salt, a dialkyldimethylammonium salt, an alkylpyridinium salt, an alkyl quarternaly ammonium salt, an alkyldimethylbenzylammonium salt, an alkylisoquinolinium salt, an dialkylmorpholinium salt, a POE alkylamine, an alkylamine salt, a fatty acid derivative of polyamine, a fatty acid derivative of amino alcohol and a quarternaly ammonium salt; amphoteric surface active agents such as an alkyl-betaine type amphoteric surface active agent, a sulfobetaine type amphoteric surface active an agent, an amidobetaine type amphoteric surface active agent, an imidazolinium-betaine type, amphoteric surface active agent and an amidoamine-type amphoteric surface active agent; nonionic surface active agents such as sorbitan fatty acid esters, glycerol or polyglycerol fatty acid esters, propylene glycol fatty acid esters, hydrogenated castor oil derivatives, glycerol alkyl ethers, POE sorbitan fatty acid esters, POE sorbitol fatty acid esters, POE glycerol fatty acid esters, POE fatty acid esters, POE alkyl ethers, POE alkyl phenyl ethers, POE-polyoxypropylene [hereinafter reffered to as "POP"] alkyl ethers, tetraPOE-tetraPOP ethylenediamine condensates, a POE castor oil or hydrogenated castor oil derivative, a POE bees wax derivative, a POE lanoline derivative, alkanolamides, a POE propylene glycol fatty acid ester, a POE alkylamine, a POE fatty acid amide, a sucrose fatty acid ester and a POE nonylphenylformaldehyde condensate, and the like.

Concrete examples of the humectant are, for instance, polyethylene glycol, propylene glycol, glycerol, 1,3-butylene glycol, diglycerol, collagen, xylitol, sorbitol, maltitol, chondroitin sulfuric acid, hyaluronic acid, mucoitin sulfate, charonin sulfric acid, cholesteryl 12-hydroxystearate, sodium lactate, a bile acid salt, a dl-pyrrolidonecarboxylic acid salt, diglycerol ethylene oxide propylene oxide adduct, elastin, keratin, casein, lecithin and the like.

Concrete examples of the antiseptic are, for instance, p-hydroxybenzoate, benzoic acid, sodium benzoate, potassium sorbate, phenoxyethanol and the like.

Concrete examples of the slicone are, for instance, a chain polysiloxane, a cyclic polysiloxane and the like.

Concrete examples of the UV-absorber are, for instance, benzoic acid derivatives, anthranilic acid dericatives, salicylic acid derivatives, cinnamic acid derivatives, benzophenone derivative and the like.

Concrete examples of the other thickeners are, for instance, karaya gum, tragacanth gum, carob gum, quince seed, casein, gelatin, sodium pectate, sodium aliginate, sodium polyacrylate, locust bean gum, guar gum, tamarind gum, dialkyldimethylammonium cellulose sulfate, magnesium aluminium silicate, bentonite, hectorite and the like.

The thus obtained cosmetic composition of the present invention imparts refreshing feeling which cannot be obtained by using a cosmetic composition containing a conventional thickener. Also, the cosmetic composition shows excellent properties such that irritation is little imparted to skin since physical properties of the cationic thickener are not deteriorated even if succinic acid, lactic acid or an amino acid which is said to be safe for skin is used, and therefore, the cosmetic composition can be used within the same pH range as human skin, that is, 4.5 to 6.5. Therefore, the cosmetic composition can be used in various forms such as cream, milky lotion, lotion, gel and foam.

When the cosmetic composition of the present invention contains various polymers for setting, flexibility is imparted to a formed film. Also, when the cosmetic composition is mixed with various raw materials for cosmetic compositions, a gel is obtained. Therefore, the cosmetic composition can be suitably used as, for instance, hair cream, hair lotion, hair treatment, hair setting gel, pack, hand cream, creamy lotion, face cleansing gel, shaving gel, hair rinse and the like.

Concrete examples of the polymer for setting are, for instance, amphoteric high molecular compounds such as compounds prepared by copolymerizing dialkylaminoethyl acrylate, dialkylaminoethyl methacrylate, diacetone acrylamide or the like with acrylic acid, methacrylic acid, alkyl acrylate, alkyl methacrylate or the like and then reacting the obtained copolymer with halogenated acetic acid to give an amphoteric compound, represented by Yukaformer AM75 commercially available from Mitsubishi Petrochemical Co., Ltd. and hydroxypropyl acrylate-butylaminoethyl methacrylate-N-octylacrylamide copolymers represented by Amphomer commercially available from National Starch & Chemical Corp.; cationic high molecular compounds such as poly(dimethyldiallylammonium halide) type cationic polymers represented by Merquat 100 commercially available from MERCK USA, cationic copolymers of dimethyldiallylammonium halide and acrylamide represented by Merquat 550 commercially avilable from MERCK USA, quaternary nitrogen atom-containing cellulose ethers represented by Polymer JR-400, Polymer JR-125 and Polymer JR-30M which are commercially available from Union Carbide Corporation, polyethylene glycol-epichlorohydrin-propylene amine-tallowylamine copolymers represented by Polyquart H commercially available from Henkel International Co., polyethylene glycol-epichlorohydrin-coconut oil alkyl amine-dipropylene triamine copolymers represented by Polyquart NH commercially available from Henkel International Co. and cationic high molecular compounds such as vinylpyrrolidone-dimethylaminoethyl methacrylate copolymers represented by H.C. Polymer 1,1N,2 and HCP-3A which are commercially available from Osaka Yuki Kagaku Kogyo Kabushiki Kaisha and GAFQUAT 755 and 734 which are commercially available from International Speciality Product Inc., anionic high molecular compounds such as copolymers of acrylic acid and/or methacrylic acid and alkyl acrylate and/or alkyl methacrylate (acrylic resin alkanolamine) represented by Aniset KB-1000, KB-100H, B-1015 and HS-3000 which are commercially available from Osaka Yuki Kagaku Kogyo Kabishiki Kaisha, Plascize L-33 and L-53 which are comercially available from Goo Chemical Co., Ltd., methyl vinyl ether-monoalkyl maleate copolymers represented by BEM-42S and WEM-225 which are commercially available from Osaka Yuki Kagaku Kogyo Kabushiki Kaisha, GANTREZ ES-425, ES-225 and ES-33 which are commercially available from International Speciality Product Inc., Resin 28-1310 and Resin 28-2930 which are commercially available from National Starch & Chemical Corp., Luviset CE5055 commercially available from Yuka Badische Co., Ltd., a copolymer of vinyl acetate and crotonic acid, an acrylic acid-alkyl acrylate-N-alkylacrylamide copolymers represented by Ultrahold 8 commercially available from Ciba-Geigy Ltd., carboxymethyl cellulose, a carboxyvinyl polymer, xanthan gum, carageenan, sodium alginate, gum arabic and pectin; nonionic high molecular compounds such as vinyl-pyrrolidone-vinyl acetate copolymers represented by PVP/VA commercially available from International Speciality Product Inc., Luviskol VA commercially available from Yuka Badische Co., Ltd., and PVA6450 commercially available from Osaka Yuki Kagaku Kogyo Kabushiki Kaisha, polyvinylpyrrolidone represented by PVPK commercially available from International Speciality Product Inc. and Luviskol K commercially available from Yuka Badische Co., Ltd., Luviflex D4101 commercially available from Yuka Badische Co., Ltd., polyvinyl alcohol, a vinyl-pyrrolidone-vinyl acetate-acrylaminoacrylate copoymer, hydroxyethyl cellulose, hydroxypropyl cellulose, hydroxypropyl methyl cellulose, methyl cellulose, ethyl cellulose, dextrin, galactan and pullulan, a copolymer of N-vinylpyrrolidone and nonquaternized dialkylaminoalkyl acrylate or methacrylate, a copolymer of vinyl caprolactam, vinylpyrrolidone and an ammonium derivative monomer, a copolymer of methyl vinyl ether and maleic anhydride, a copolymer of vinyl acetate, n-butyl maleate and isobornyl acrylate, a copolymer of vinyl pyrrolidone and an ammonium derivative monomer, and the like.

When a viscous liquid hair dressing agent is prepared by using the cationic thickener, it is desired that the viscosity of the hair dressing agent at 25° C. when using a BH-type Brookfield viscometer (Rotor No. 4) is 500 to 10,000 cP. Also, when a gelatinous hair dressing agent is prepared, it is desired that the viscosity of the hair dressing agent at 25° C. is 10,000 to 50,000 cP.

The cosmetic composition comprising the cationic thickener of the present invention is more specifically described and explained by means of the following Examples. It is to be understood that the present invention is not limited to the Examples.

PREPARATIVE EXAMPLE 1

To a four-necked flask equipped with a mechanical stirrer, a thermometer, a reflux condenser and a tube for introducing nitrogen gas, 50 g of N,N-dimethylaminoethyl methacrylate, 47.5 g of N-vinylpyrrolidone, 2.5 g of stearyl acrylate and 1.9 g of tripropylene glycol diacrylate, and a mixture of 23.1 g of ethanol and 554.3 g of cyclohexane (the weight ratio of the ethanol/cyclohexane: 4/96) were added. Then, the obtained mixture was stirred with refluxing at 80° C. for 2 hours in a stream of nitrogen gas to degas.

Then, 0.41 g of 2,2'-azobisisobutyronitrile was added to the four-necked flask to initiate the polymerization at 80° C. After 45 minutes passed from the initiation of the polymerization, 1.9 g of tripropyleneglycol diacrylate was added thereto. After further 45 minutes passed, 1.9 g of tripropyleneglycol diacrylate was added thereto. The polymerization reaction was carried out for about 10 hours with stirring in a stream of nitrogen gas. Then, the obtained polymer slurry solution was filtrated under reduced pressure and the obtained solid was dried under reduced pressure.

The obtained dried polymer was pulverized with a pulverizer to obtain a white powdered cationic thickener.

Then, distilled water was added to the cationic thickener so that the concentration of the cationic thickener became 1% by weight, and its pH was adjusted by using lactic acid as a neutralizer. The mixture was stirred for about 5 hours by using a stirrer equipped with a propeller blade to obtain a transparent gel.

As the physical properties of the obtained gel, viscosity, feel, appearance, flexibility of a formed film and gloss of a formed film were investigated in accordance with the following methods. The results are shown in Table 1.

(A) Viscosity

The viscosity was measured at a temperature of 20° C., using a BH-type (Rotor No. 4, rotation: 20 rpm) Brookfield viscometer commercially available from Tokyo Keiki Co., Ltd.

(B) Feel

The feel was examined by holding about 2 ml of the obtained gel between fingers and rubbing the gel. The feel was evaluated in accordance with the following criteria for evaluation.

[Criteria for evaluation]

A: Smooth and light feeling

B: A little rough feeling

C: Somewhat rough feeling

D: Remarkably rough feeling (C) Appearance

Whether the obtained gel was contaminated with impurities or not was examined by observing the obtained gel with naked eyes. The appearance was evaluated in accordance with the following criteria for evaluation.

[Criteria for evaluation]

A: No contamination of impurities was observed.

B: A little contamination of impurities was observed.

C: Contamination of impurities was somewhat observed.

D: Contamination of impurities was remarkably observed.

(D) Flexibility of a formed film

The obtained gel was coated on a film made of a vinyl chloride resin by using a bar coater so that a film of the gel having a thickness of 10 μm could be obtained. A film was formed by air drying for 3 hours, and the film made of the vinyl chloride resin was randomly bent. The state of the formed film of the gel was observed. Then, the flexibility was evaluated in accordance with the following criteria for evaluation.

[Criteria for evaluation]

A: No change was observed.

B: Peeling was slightly observed.

C: Peeling was observed in part.

D: Perfect peeling was observed.

(E) Gloss of a formed film

The film which was formed in the above-mentioned item (D) was observed with naked eyes. The gloss was evaluated in accordance with the following criteria for evaluation.

[Criteria for evaluation]

A: The film had a gloss.

B: The film had a little gloss.

C: The film had no gloss.

PREPARATIVE EXAMPLE 2 to 4

White powdered cationic thickeners were obtained in the same manner as in Preparative Example 1 except that monomers containing (meth)acryloyl group as shown in Table 1 were used instead of stearyl acrylate.

Then, gels were prepared by using the obtained cationic thickener in the same manner as in Preparative Example 1, and the physical properties thereof were examined. The results are shown in Table 1.

PREPARATIVE EXAMPLE 5

A white powdered cationic thickener was obtained in the same manner as in Preparative Example 1 except that N,N-dimethylaminopropylmethacrylamide was used instead of N, N-dimethylaminoethyl methacrylate.

Then, a gel was prepared by using the obtained cationic thickener in the same manner as in Preparative Example 1, and the physical properties thereof were examined. The results are shown in Table 1.

PREPARATIVE EXAMPLE 6

To a four-necked flask equipped with a mechanical stirrer, a thermometer, a reflux condenser and a tube for introducing nitrogen gas, 50 g of N,N-dimethylaminoethyl methacrylate, 47.5 g of methacrylamide, 2.5 g of stearyl acrylate and 1.9 g of tripropyleneglycol diacrylate were added as monomers, and the concentration of the monomers was adjusted so as to become 21% by weight by adding 376.2 g of ethanol thereto. Then, the obtained mixture was stirred for 2 hours in a stream of nitrogen gas with refluxing at 80° C. to degas the mixture.

Then, 0.41 g of 2,2,-azobisisobutyronitrile was added to the four-necked flask, and the polymerization was initiated at 80° C. After 45 minutes passed from the initiation of the polymerization, 1.9 g of tripropyleneglycol diacrylate was added to the four-necked flask, and after further 45 minutes passed, 1.9 g of tripropyleneglycol diacrylate was added to the four-necked flask. The polymerization reaction was carried out for about 10 hours with stirring in a stream of nitrogen gas. After that, the obtained polymer slurry solution was filtrated under reduced pressure, and the obtained solid was dried under reduced pressure.

The dried polymer was pulverized by using a pulverizer to obtain a white powdered cationic thickener. A gel was prepared using the obtained cationic thickener in the same manner as in Preparative Example 1 and then the physical properties thereof were examined. The results are also shown in Table 1.

PREPARATIVE EXAMPLES 7 to 10

White powdered cationic thickeners were obtained using raw materials shown in Table 1 in the same manner as in Preparative Example 1.

Then, gels were prepared using the obtained cationic thickeners in the same manner as in Preparative Example 1, and the physical properties thereof were examined. The results are also shown in Table 1.

PREPARATIVE EXAMPLES 11 and 12

White powederd cationic thickeners were obtained using raw materials shown in Table 1 in the same manner as in Preparative Example 1 except that the amount of tripropyleneglycol diacrylate was divided into three, and the divided tripropyleneglycol diacrylate was added to the four-necked flask in the same manner as in Preparative Example 1.

Then, gels were prepared using the obtained cationic thickeners in the same manner as in Preparative Example 1, and the physical properties thereof were examined. The results are shown in Table 1.

PREPARATIVE EXAMPLES 13 to 18

White powdered cationic thickeners were obtained using raw materials shown in Table 1 in the same manner as in Preparative Example 1.

Then, gels were prepared using the obtained cationic thickeners in the same manner as in Preparative Example 1, and the physical properties thereof were examined. The results are also shown in Table 1.

TABLE 1

| Preparative Example No. | Components of monomer composition for a thickener (g) | | | | | |
|---|---|---|---|---|---|---|
| | (Meth)acrylic monomer having an amino group | Vinyl monomer | Monomer having (meth)acryloyl group | Crosslinkable vinyl monomer | Solvent (g) Good solvent | Bad solvent |
| 1 | NDAEMA (50) | NVP (47.5) | STA (2.5) | TPGDA (5.7) | ET (23.1) | CH (554.3) |
| 2 | NDAEMA (50) | NVP (47.5) | LMA (2.5) | TPGDA (5.7) | ET (23.1) | CH (554.3) |
| 3 | NDAEMA (50) | NVP (47.5) | NOAA (2.5) | TPGDA (5.7) | ET (23.1) | CH (554.3) |
| 4 | NDAEMA (50) | NVP (47.5) | MPEGMA (2.5) | TPGDA (5.7) | ET (23.1) | CH (554.3) |
| 5 | NDAPMA (50) | NVP (47.5) | STA (2.5) | TPGDA (5.7) | ET (23.1) | CH (554.3) |
| 6 | NDAEMA (50) | MAA (47.5) | STA (2.5) | TPGDA (5.7) | ET (376.2) | — |
| 7 | NDAEMA (21.1) | NVP (76.3) | STA (2.5) | TPGDA (5.7) | ET (23.1) | CH (554.3) |
| 8 | NDAEMA (84.6) | NVP (12.9) | STA (2.5) | TPGDA (5.7) | ET (23.1) | CH (554.3) |
| 9 | NDAEMA (35.4) | NVP (32.9) | STA (31.7) | TPGDA (5.7) | ET (23.1) | CH (554.3) |
| 10 | NDAEMA (35.4) | NVP (6.5) | STA (58.1) | TPGDA (5.7) | ET (23.1) | CH (554.3) |
| 11 | NDAEMA (50) | NVP (42.6) | STA (2.5) | TPGDA (10.5) | ET (23.1) | CH (554.3) |
| 12 | NDAEMA (50) | NVP (37.3) | STA (2.5) | TPGDA (15.9) | ET (23.1) | CH (554.3) |
| 13 | NDAEMA (50) | NVP (47.5) | LA (2.5) | TPGDA (5.7) | ET (23.1) | CH (554.3) |
| 14 | NDAEMA (50) | NVP (47.5) | BA (2.5) | TPGDA (5.7) | ET (23.1) | CH (554.3) |
| 15 | NDAEMA (50) | NVP (50) | — | TPGDA (5.7) | ET (23.1) | CH (554.3) |
| 16 | NDAEMA (50) | NVP (47.5) | STA (2.5) | TPGDA (7.5) | ET (21.3) | CH (587.8) |
| 17 | NDAEMA (50) | NVP (47.5) | STA (2.5) | TPGDA (7.5) | ET (21.3) | CH (587.8) |
| 18 | NDAEMA (50) | NVP (47.5) | STA (2.5) | TPGDA (7.5) | ET (43.0) | CH (387.0) |

| Preparative Example No. | Concentration of monomer composition for a thickener (% by weight) | Polymerization catalyst (g) | Physical properties of gel | | | |
|---|---|---|---|---|---|---|
| | | | Viscosity (cP) | Feel | Appearance | Flexibility of formed | Gloss of formed |
| 1 | 15 | AIBN (0.41) | 2300 | A | A | A | A |
| 2 | 15 | AIBN (0.41) | 2500 | A | A | A | A |
| 3 | 15 | AIBN (0.41) | 2700 | A | A | A | A |
| 4 | 15 | AIBN (0.41) | 2000 | A | A | A | A |
| 5 | 15 | AIBN (0.41) | 2000 | A | A | A | A |
| 6 | 22 | AIBN (0.41) | 1500 | A | A | A | A |
| 7 | 15 | AIBN (0.41) | 1100 | A | A | A | A |
| 8 | 15 | AIBN | 4000 | A | A | A | A |

TABLE 1-continued

| | | | | | | | |
|---|---|---|---|---|---|---|---|
| 9 | 15 | AIBN (0.41) | 2100 | A | A | A | A |
| 10 | 15 | AIBN (0.41) | 2300 | A | A | A | A |
| 11 | 15 | AIBN (0.41) | 3100 | A | A | A | A |
| 12 | 15 | AIBN (0.41) | 3900 | A | A | A | A |
| 13 | 15 | AIBN (0.41) | 2600 | A | A | A | A |
| 14 | 15 | AIBN (0.41) | 2300 | B | A | B | B |
| 15 | 15 | AIBN (0.41) | 2000 | B | A | B | B |
| 16 | 15 | DAMP (0.38) | 6900 | A | A | A | A |
| 17 | 15 | TBPO (0.64) | 11000 | A | A | A | A |
| 18 | 20 | AIBN (0.32) | 17200 | B | A | A | A |

In the Table 1, each abbreviation is intended to refer to the following compounds.
NDAEMA: N,N-dimethylaminoethyl methacrylate
NDAPMA: N,N-dimethylaminopropylmethacrylamide
NVP: N-vinylpyrrolidone
MAA: methacrylamide
STA: stearyl acrylate
LMA: lauryl methacrylate
NOAA: N-t-octylacrylamide
MPEGMA: methoxypolyethylene glycol (23) methacrylate
TPGDA: tripropyleneglycol diacrylate
ET: ethanol
CH: cyclohexane
AIBN: 2,2'-azobisisobutyronitrile
LA: Lauryl acrylate
BA: n-Buryl acrylate
DAMP: Dimethyl 2,2'-Azobis(2-methylpropionate)
TBPO: t-Butylperoxy 2-ethylhexanoate

EXPERIMENTAL EXAMPLE 1

To the cationic thickener obtained in Preparative Example 1, distilled water was added to give a 1% polymer slurry solution. The relation between pH and viscosity was examined at a temperature of 20° C. using a BH-type Brookfield viscometer (rotor No. 4) and lactic acid as a neutralizer. The results are shown in FIG. 1.

In FIG. 1, the rotation was carried out at 4 rpm in A, at 10 rpm in B and at 20 rpm in C, respectively.

From the results shown in FIG. 1, it can be seen that the polymer slurry solution prepared by using the obtained cationic thickener shows high viscosity within almost the same pH range as human skin (4.5 to 6.5).

EXPERIMENTAL EXAMPLE 2

To the cationic thickener obtained in Preparative Example 1, distilled water was added to prepare a 1% polymer slurry solution, and the pH was adjusted to 7.0 by adding lactic acid as a neutralizer. The fluctuation of viscosity with temperature was measured using a BH-type Brookfield viscometer (rotor No. 4). The results are shown in FIG. 2.

Figure 2:
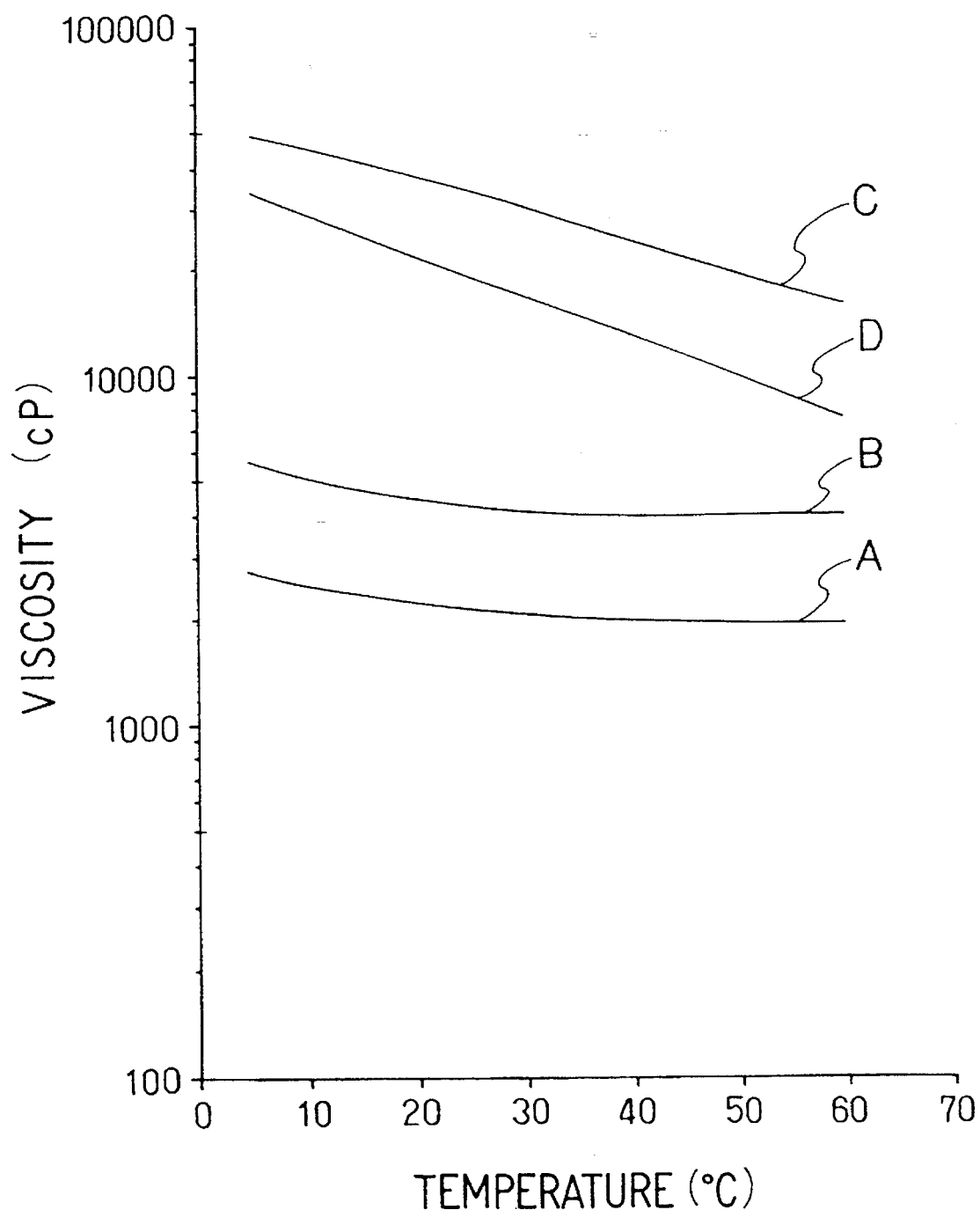
FIG. 2 is a graph showing fluctuations of viscosity of a 1% slurry solution of a polymer, a 0.5% aqueous solution of CARBOPOL, a 2.5% aqueous solution of sodium alginate and a 2.0% aqueous solution of carboxymethyl cellulose obtained in Experiment 2 accoring to the present invention with temperature.

In FIG. 2, A, B, C and D denote variations of viscosity with temperature when a 1% slurry solution of the cationic thickener obtained in Preparative Example 1, as an anionic synthetic thickener, a 0.5% CARBOPOL commercially available from BF. Good Rich Company (trade name) aqueous solution, a 2.5% aqueous solution of sodium alginate and a 2.0% aqueous solution of carboxymethyl cellulose were used, respectively.

The pH of the obtained aqueous solution was adjusted to 7 with lactic acid or sodium hydroxide as occasion demands.

From the results shown in FIG. 2, it can be seen that CARBOPOL which is a synthetic high molecular compound and the cationic thickener show smaller change of viscosity over a wide range of temperatures and higher thermal stability in comparison with sodium alginate which is a natural high molecualr compound.

From this fact, it can be seen that the cationic thickener can be suitably used in cosmetic compositions for which stable quality is required over a wide range of temperatures.

EXPERIMENTAL EXAMPLE 3

Using the cationic thickener obtained in Preparative Example 1 and lactic acid which is a hydrophilic organic acid and stearic acid which is a lipophilic organic acid as neutralizers, ability of gelation against various solvents was examined in accordance with the following method, and the appearance of the obtained gel was observed with naked eyes. The results are shown in Table 2.
(A) Ability of gelation A glass test tube having an inside diameter of 20 mm was charged with 1 g of a cationic thickener, and a neutralizer shown in Table 2 was added thereto. After that, a solvent shown in Table 2 was added thereto with stirring until the mixture exhibited fluidity when the test tube was inclined to an angle of 45°. At that time, the amount of the solvent was measured, and the ability of gelation was calculated in accordance with the equation:

$$\text{Ability of gelatin (times)} = \frac{\text{Amount of the solvent (g)}}{\text{Amount of the cationic thickener (g)}} \times 100.$$

[Creteria for evaluation]
A: Transparency and no cloudiness were observed.
B: Transparency and a little cloudiness were observed.
C: Turbidity or cloudiness was obviously observed.

TABLE 2

| Preparative Example No. | Solvent | Neutralizer (Amount (g)) | Ability of gelation (Times) | Appearance of gel |
|---|---|---|---|---|
| 1 | n-Hexane | Lactic acid (0.30) | Gel was not generated. | — |
| 2 | n-Hexane | Stearic acid (0.84) | 20 | White ununiform gel |
| 3 | Cyclohexane | Lactic acid (0.30) | Gel was not generated. | — |
| 4 | Cyclohexane | Stearic acid (0.84) | 25 | White ununiform gel |
| 5 | Benzene | Lactic acid (0.30) | Gel was not generated. | — |
| 6 | Benzene | Stearic acid (0.84) | 35 | Transparent |
| 7 | Toluene | Lactic acid (0.30) | Gel was not generated. | — |
| 8 | Toluene | Stearic acid (0.84) | 35 | Transparent |
| 9 | Ethyl acetate | Lactic acid (0.30) | Gel was not generated. | — |
| 10 | Ethyl acetate | Stearic acid (0.84) | 15 | Transparent |
| 11 | Diethyl phthalate | Lactic acid (0.30) | Gel was not generated. | — |
| 12 | Diethyl phthalate | Stearic acid (0.84) | 30 | Transparent |
| 13 | Ethanol | Lactic acid (0.30) | 50 | Transparent |
| 14 | Ethanol | Stearic acid (0.84) | 35 | Transparent |
| 15 | Ethylene glycol | Lactic acid (0.30) | 135 | Transparent |
| 16 | Ethylene glycol | Stearic acid (0.84) | 65 | Transparent |
| 17 | γ-Butyrolactone | Lactic acid (0.30) | 75 | Transparent |
| 18 | γ-Butyrolactone | Stearic acid (0.84) | 30 | Approximately transparent |
| 19 | Dichloromethane | Lactic acid (0.30) | Gel was not generated. | — |
| 20 | Dichloromethane | Stearic acid (0.84) | 35 | Transparent |
| 21 | Distilled water | Lactic acid (0.30) | 75 | Transparent |
| 22 | Distilled water | Stearic acid (0.89) | Gel was not generated. | — |

From the results shown in Table 2, it can be seen that the hydrophilic organic acid such as lactic acid is preferably used as a neutralizer when the hydrophilic solvent is gelled with the cationic thickener.

On the other hand, it can be seen that the lipophilic organic acid such as stearic acid is preferably used as a neutralizer when the lipophilic solvent is gelled with the cationic thickener.

Also, from the results shown in Table 2, it can be seen that the cationic thickener can be widely used in cosmetic compositions since various solvents can be gelled by selecting an acid from various acids for neutralizing.

EXPERIMENTAL EXAMPLE 4

The cationic thickener obtained in Preparative Example 1, Preparative Example 13, Preparative Example 14 or Preparative Example 15 was added to distilled water in a ratio shown in Table 3 to give a polymer slurry solution.

After the pH of the obtained polymer slurry solution was adjusted to 4.5 to 5.0 with lactic acid, an additive shown in Table 3 was added thereto in the amount shown in Table 3 to give a gel in the amount of 100 g.

Also, after the pH of the obtained polymer slurry solution was adjusted to 4.5 to 5.0 with lactic acid, distilled water was added thereto instead of an additive to give a gel in the amount of 100 g, which was used as a blank for measuring salt water resistance.

The appearance and salt water resistance of the obtained gel were examined in accordance with the following methods.

(A) Appearance

The appearance of the obtained gel was observed with naked eyes, and evaluated in accordance with the following criteria for evaluation.

D: Milky cloudiness or precipitate was observed.

(B) Salt water resistance

The viscosity of an obtained gel and its blank was measured at a temperature of 20° C., using a BH-type (Rotor No. 4, rotation: 20 rpm) Brookfield viscometer commercially available from Tokyo Keiki Co., Ltd.

The salt water resistance was calculated in accordance with the following equation.

(Salt water resistance)=(Viscosity of a gel)×100/(Viscosity of blank) (%)

TABLE 3

| Experimental No. | Components of polymer slurry solution (g) | | Additive | | Concentration of additive in water (% by weight) | Physical properties | |
|---|---|---|---|---|---|---|---|
| | Cationic thickener | Distilled water | Kind | Amount (g) | | Appearance | Salt water resistance (%) |
| 1 | Cationic thickener obtained in Preparative Example 1 (3) | (87) | NaCl | 10 | 3 | A | 95 |
| 2 | Cationic thickener obtained in Preparative Example 13 (3) | (87) | NaCl | 10 | 3 | A | 95 |
| 3 | Cationic thickener obtained in Preparative Example 14 (3) | (87) | NaCl | 10 | 3 | B | 45 |
| 4 | Cationic thickener obtained in Preparative Example 15 (3) | (87) | NaCl | 10 | 3 | B | 44 |
| 5 | Cationic thickener obtained in Preparative Example 1 (3) | (87) | CaCl$_2$ | 10 | 3 | A | 95 |
| 6 | Cationic thickener obtained in Preparative Example 13 (3) | (87) | CaCl$_2$ | 10 | 3 | A | 73 |
| 7 | Cationic thickener obtained in Preparative Example 14 (3) | (87) | CaCl$_2$ | 10 | 3 | B | 48 |
| 8 | Cationic thickener obtained in Preparative Example 15 (3) | (87) | CaCl$_2$ | 10 | 3 | B | 51 |
| 9 | Cationic thickener obtained in Preparative Example 1 (3) | (77) | NaLS | 20 | 3 | A | 224 |
| 10 | Cationic thickener obtained in Preparative Example 13 (3) | (77) | NaLS | 20 | 3 | A | 130 |
| 11 | Cationic thickener obtained in Preparative Example 14 (3) | (77) | NaLS | 20 | 3 | B | 43 |
| 12 | Cationic thickener obtained in Preparative Example 15 (3) | (77) | NaLS | 20 | 3 | B | 44 |
| 13 | Cationic thickener obtained in Preparative Example 1 (3) | (77) | NCTAB | 20 | 3 | A | 106 |
| 14 | Cationic thickener obtained in Preparative Example 13 (3) | (77) | NCTAB | 20 | 3 | A | 96 |
| 15 | Cationic thickener obtained in Preparative Example 14 (3) | (77) | NCTAB | 20 | 3 | A | 70 |
| 16 | Cationic thickener obtained in Preparative Example 15 (3) | (77) | NCTAB | 20 | 3 | A | 75 |

(Note)
NaLS: Sodium lauryl sulfate
NCTAB: N-cetyltrimethylammonium bromide

From the results shown in Table 3, it can be seen that the gels obtained in Preparative Examples 1 and 13 show high salt water resistance.

On the other hand, it can be seen that the gel obtained in Preparative Examples 14 and 15 do not show high salt water resistance since as to Preparative Example 14, a monomer having a short chain acryloyl group is used, and as to Preparative Example 15, a monomer having at least one of acryloyl group and methacryloyl group is not used.

EXAMPLES 1 To 24 AND COMPARATIVE
EXAMPLES 1 TO 6

The cationic thickener which was obtained in Preparative Example 1, Preparative Example 3, Preparative Example 5 or Preparative Example 6, Preparative Example 14 or Preparative Example 15 was mixed with distilled water and ethanol in the amount shown in Table 4, and then its pH was adjusted to 6.5 by using lactic acid.

As a setting polymer, a nonionic polymer for setting (N-vinylpyrrolidone-vinyl acetate copolymer commercially available from Osaka Yuki Kagaku Kogyo Kabushiki Kaisha under the trade name of PVA-6450), a cationic polymer for setting (diethyl sulfate of N-vinylpyrrolidone-N, N-dimethylaminoethyl methacrylate copolymer commercially available from Osaka Yuki Kagaku Kogyo Kabushiki Kaisha under the trade name of HCP-3A) and an amphoteric polymer for setting (N-methacryloyl-ethyl-N,N-dimethylammonium-α-N-methylcarboxybetaine-methacrylic acid ester copolymer commercially available from Mitsubishi Petrochemical Co., Ltd., under the trade name of Yukaformer AM75) was gradually added thereto in the amount shown in Table 4. The mixture was stirred by using a stirrer equipped with a propeller blade until the mixture became uniform to give a setting gel for hair.

As the physical properties of the obtained setting gel, viscosity, transparency, setting property, feel, flaking and facility for shampooing were examined in accordance with the following methods. The results are shown in Table 4.

(A) Viscosity

The viscosity was measured at a temperature of 25° C. by using a BH-type Brookfield viscometer commercially available from Tokyo Keiki Co., Ltd. (rotor No. 4) at 20 rpm.

(B) Transparency

Thirty grams of the obtained setting gel was weighed and a glass cell for measuring turbidity was charged with the setting gel. After the gel was defoamed at room temperature for 1 hour by using an ultrasonic cleaner, the glass cell was set in a 18900-00 type Ratio turbidimeter commercially available from HACH COMPANY and allowed to stand for 15 minutes for stabilizing the measured value. Then, the value of turbidity was read off and the transparency was evaluated in accordance with the following criteria for evaluation.

[Criteria for evaluation]

A: Less than 3 NTU

B: At least 3 NTU and less than 5 NTU

C: At least 5 NTU (C) Setting property

The obtained setting gel was uniformly applied in the amount of 3 g to 2 g of hair having a length of 25 cm with hand. This hair was wound around a curler having an outside diameter of 1.2 cm, and the hair was dried by hot air of 40° C. for 60 minutes. Then, the hair was removed from the curler and the hair was perpendicularly hung in an atmosphere having a relative humidity of 80% and a temperature of 30° C. The length just after hanging (L 1) and the length after hanging for 1 hour (L2) were measured and the curl retention value was calculated in accordance with the equation:

$$\text{(Curl retention value)} = \frac{25 - L2}{25 - L1} \times 100 \, (\%).$$

The greater the curl retention value is, the better the setting property is. In the present invention, when the curl retention value is at least 60%, the setting gel can be satisfactorily used.

(D) Feel

The feel was examined by holding about 2 ml of the obtained setting gel between fingers and rubbing the setting gel. The feel was evaluated in accordance with the following criteria for evaluation.

[Criteria for evaluation]

A: Smooth and light feeling

B: Little rough feeling

C: Somewhat rough feeling

D: Remarkably rough feeling (E) Flaking

The setting gel was uniformly applied in the amount of 3 g to hair having a length of 25 cm and the excessive gel was removed by stroking with hand.

This hair was dried by hot air of 40° C. for 60 minutes to form a film on the surface of the hair, and the hair was combed 10 times by using a comb. Then, the film was evaluated in accordance with the following criteria for evaluation.

[Criteria for evaluation]

A: No peeling was observed.

B: Peeling was observed in part.

C: Peeling was observed throughout.

(F) Facility for shampooing

The setting gel was uniformly applied in the amount of 3 g to hair having a length of 25 cm, and the excessive gel was removed by stroking with hand. After the hair was dried by hot air of 40° C. for 60 minutes, the hair was soaked in warm water containing 0.5% of a marketed shampoo having a tenperature of 30° C., and the warm water was stirred. The condition of the removal of the setting gel was observed after 30 minutes or 40 minutes passed, and the facility for shampooing was evaluated in accordance with the following criteria for evaluation.

[Criteria for evaluation]

A: Within 30 minutes the setting gel could be completely removed by washing without slime.

B: Within 40 minutes the setting gel could be completely removed by washing without slime.

C: After 40 minutes passed, the setting gel somewhat remained and a little slime was observed.

D: The setting gel could not be removed by washing and slime remained after 40 minutes passed.

TABLE 4

| Example No. | Components of setting gel (g) | | | | Physical properties of setting gel | | | | | |
|---|---|---|---|---|---|---|---|---|---|---|
| | Cationic thickener | Distilled water | Ethanol | Polymer for setting | Viscosity (cP) | Transparency | Setting property (%) | Feel | Flaking | Facility for shampooing |
| 1 | Cationic thickener obtained in Preparative Example 1 (3.5) | (66.5) | (10) | Nonionic polymer for setting (14) | 3900 | A | 75 | A | A | A |
| 2 | Cationic thickener obtained in Preparative Example 3 (3.5) | (66.5) | (10) | Nonionic polymer for setting (14) | 3800 | A | 75 | A | A | A |
| 3 | Cationic thickener obtained in Preparative Example 5 (3.5) | (66.5) | (10) | Nonionic polymer for setting (14) | 3200 | A | 80 | A | A | A |
| 4 | Cationic thickener obtained in Preparative Example 6 (3.5) | (66.5) | (10) | Nonionic polymer for setting (14) | 2900 | A | 88 | A | A | A |
| 5 | Cationic thickener | (66) | (10) | Nonionic | 4000 | A | 82 | A | A | A |

TABLE 4-continued

| | | Components of setting gel (g) | | | Physical properties of setting gel | | | | | |
|---|---|---|---|---|---|---|---|---|---|---|
| | Cationic thickener | Distilled water | Ethanol | Polymer for setting | Viscosity (cP) | Trans- parency | Setting property (%) | Feel | Flaking | Facility for shampooing |
| 6 | Cationic thickener obtained in Preparative Example 1 (4) | (66) | (10) | Nonionic polymer for setting (20) | 3700 | A | 84 | A | A | A |
| 7 | Cationic thickener obtained in Preparative Example 3 (4) | (66) | (10) | Nonionic polymer for setting (20) | 3400 | A | 88 | A | A | A |
| 8 | Cationic thickener obtained in Preparative Example 5 (4) | (66) | (10) | Nonionic polymer for setting (20) | 3000 | A | 91 | A | A | A |
| 9 | Cationic thickener obtained in Preparative Example 6 (4) | (66.5) | (10) | Cationic polymer for setting (14) | 3200 | A | 72 | A | A | A |
| 10 | Cationic thickener obtained in Preparative Example 1 (3.5) | (66.5) | (10) | Cationic polymer for setting (14) | 3000 | A | 74 | A | A | A |
| 11 | Cationic thickener obtained in Preparative Example 3 (3.5) | (66.5) | (10) | Cationic polymer for setting (14) | 2800 | A | 77 | A | A | A |
| 12 | Cationic thickener obtained in Preparative Example 5 (3.5) | (66.5) | (10) | Cationic polymer for setting (14) | 2500 | A | 80 | A | A | A |
| 13 | Cationic thickener obtained in Preparative Example 6 (3.5) | (66) | (10) | Cationic polymer for setting (20) | 3000 | A | 80 | A | A | A |
| 14 | Cationic thickener obtained in Preparative Example 1 (4) | (66) | (10) | Cationic polymer for setting (20) | 2800 | A | 80 | A | A | A |
| 15 | Cationic thickener obtained in Preparative Example 3 (4) | (66) | (10) | Cationic polymer for setting (20) | 2500 | A | 86 | A | A | A |
| 16 | Cationic thickener obtained in Preparative Example 5 (4) | (66) | (10) | Cationic polymer for setting (20) | 2100 | A | 89 | A | A | A |
| 17 | Cationic thickener obtained in Preparative Example 6 (4) | (66.5) | (10) | Amphoteric polymer for setting (14) | 3300 | A | 79 | A | A | A |
| 18 | Cationic thickener obtained in Preparative Example 1 (3.5) | (66.5) | (10) | Amphoteric polymer for setting (14) | 3200 | A | 78 | A | A | A |
| 19 | Cationic thickener obtained in Preparative Example 3 (3.5) | (66.5) | (10) | Amphoteric polymer for setting (14) | 3200 | A | 79 | A | A | A |
| 20 | Cationic thickener obtained in Preparative Example 5 (3.5) | (66.5) | (10) | Amphoteric polymer for setting (14) | 3000 | A | 81 | A | A | A |
| 21 | Cationic thickener obtained in Preparative Example 6 (3.5) | (66) | (10) | Amphoteric polymer for setting (20) | 3200 | A | 85 | A | A | A |
| 22 | Cationic thickener obtained in Preparative Example 1 (4) | (66) | (10) | Amphoteric polymer for setting (20) | 3000 | A | 84 | A | A | A |
| 23 | Cationic thickener obtained in Preparative Example 3 (4) | (66) | (10) | Amphoteric polymer for setting (20) | 2800 | A | 85 | A | A | A |
| 24 | Cationic thickener obtained in Preparative Example 5 (4) | (66) | (10) | Amphoteric polymer for setting (20) | 2500 | A | 87 | A | A | A |
| Com. Ex. No. | | | | | | | | | | |
| 1 | Cationic thickener obtained in Preparative Example 14 (4) | (66) | (10) | Nonionic polymer for setting (20) | 4300 | A | 75 | B | B | A |
| 2 | Cationic thickener obtained in Preparative Example 15 (4) | (66) | (10) | Nonionic polymer for setting (20) | 3700 | A | 73 | B | B | A |
| 3 | Cationic thickener obtained in Preparative Example 14 (4) | (66) | (10) | Cationic polymer for setting (20) | 2900 | A | 79 | B | B | A |
| 4 | Cationic thickener obtained in Preparative Example 15 (4) | (66) | (10) | Cationic polymer for setting (20) | 3000 | A | 73 | B | B | A |

TABLE 4-continued

| | | Components of setting gel (g) | | | Physical properties of setting gel | | | | | |
|---|---|---|---|---|---|---|---|---|---|---|
| | Cationic thickener | Distilled water | Ethanol | Polymer for setting | Viscosity (cP) | Trans-parency | Setting property (%) | Feel | Flaking | Facility for shampooing |
| 5 | Cationic thickener obtained in Preparative Example 14 (4) | (66) | (10) | Amphoteric polymer for setting (20) | 2400 | C | 80 | B | A | A |
| 6 | Cationic thickener obtained in Preparative Example 15 (4) | (66) | (10) | Amphoteric polymer for setting (20) | 1900 | C | 75 | B | A | A |

From the results shown in Table 4, it can be seen that a gel for hair setting can be prepared even though any of nonionic, cationic and amphoteric polymers for setting is used when the cationic thickener used in Examples 1 to 24 according to the present invention is used, and that the obtained setting gel for hair (cosmetic composition) is excellent in the physical properties such as facility for shampooing and setting property.

EXAMPLE 25

To 4 g of the cationic thickener obtained in Preparative example 1, a solution prepared by dissolving 15 g of polyvinyl alcohol in 66 g of purified water and 10 g of ethyl alcohol was added to prepare a uniform dispersion. After its pH was adjusted to 6.5 by adding lactic acid to the dispersion, a desired amount of a perfume and antiseptic and 5 g of glycerol were added thereto. Then, the obtained mixture was uniformly mixed and defoamed by stirring under reduced pressure to give a facial mask.

A monitoring test was carried out as to feeling when the obtained facial mask was used by 10 women in their twenties who have ever used a conventional facial mask. The results are evaluated in accordance with the following criteria for evaluation. The results are shown in Table 5.
[Criteria for evaluation]
  A: Excellent refreshing feeling and no stickiness were imparted.
  B: Relatively little stickiness was imparted, and feeling was good.
  C: No feeling was especially observed.
  D: Stickiness was great and feeling was bad.

TABLE 5

| | Feeling when facial mask was used (Number of persons) | | | |
|---|---|---|---|---|
| Example No. | A | B | C | D |
| 25 | 5 | 4 | 1 | 0 |

In Table 5, the "C" level shows the level of conventional facial mask. From the results shown in Table 5, it can be seen that the obtained facial mask containing the cationic thickener shows little stickiness and imparts excellent feeling to users.

EXAMPLE 26

To 2.5 g of the cationic thickener obtained in Preparative Example 1, 57.5 g of purified water was added and the obtained mixture was stirred to prepare a uniform dispersion. This dispersion was heated to 60° C., and 10.0 g of bees wax and 30.0 g of liquid paraffin were gradually added thereto, and its pH was adjusted to 6.0 by adding lactic acid thereto. The obtained mixture was uniformly mixed and defoamed by stirring under reduced pressure to give hand cream.

A monitoring test was carried out as to feeling when the obtained hand cream was used by 10 men and 10 women in their twenties who have ever used conventional hand cream. The results are evaluated in accordance with the following criteria for evaluation. The results are shown in Table 6.
[Criteria for evaluation]
  A: The hand cream could be widely spread, and excellent refreshing feeling was omparted.
  B: Relatively little stickiness and excellent refreshing feeling were imparted.
  C: No feeling was especially obvserved.
  D: Stickiness was great and feeling was bad.

TABLE 6

| | Feeling when hand cream was used (Number of persons) | | | |
|---|---|---|---|---|
| Example No. | A | B | C | D |
| 26 | 10 | 6 | 4 | 0 |

In Table 6, the "C" level shows the level of conventional hand cream. From the results shown in Table 6, it can be seen that the obtained hand cream containing the cationic thickener imparts excellent refreshing feeling.

EXAMPLE 27

To 1.0 g of the cationic thickener obtained in Preparative Example 1, 65.0 g of purified water was added and stirred to prepare a uniform dispersion. The dispersion was heated to 70° C., and a mixture of 3.0 g of bees was, 15.0 g of vaseline, 10.0 g of liquid paraffin, 3.0 g of polyoxyethylene (5) stearate, 2.0 g of polyoxyethylene (6) oleyl alcohol and 1.0 g of polyoxyethylene cetyl alcohol was gradually added thereto. Then, its pH was adjusted by adding lactic acid to 6.0 to obtain hair cream.

A monitoring test was carried out as to feeling when the obtained hair cream was used by 10 women in their twenties who have ever used conventional hair cream. The results are evaluated in accordance with the following criteria for evaluation. The results are shown in Table 7.
[Criteria for evaluation]
  A: Little stickiness was observed and hair could be easily conditioned.
  B: A little stickiness was observed but hair could be easily conditioned.

C: No feeling was especially observed.

D: Stickiness was great and hair could not be easily conditioned.

TABLE 7

| | Feeling when hair cream was used (Number of persons) | | | |
|---|---|---|---|---|
| Example No. | A | B | C | D |
| 27 | 6 | 3 | 1 | 0 |

In Table 7, the "C" level shows the level of the conventional hair cream. From the results shown in Table 7, it can be seen that the obtained hair cream containing the cationic thickener shows little stickiness and imparts excellent feeling, and hair can be easily conditioned.

EXAMPLE 28

To 2.0 g of the cationic thickener obtained in Preparative Example 1, 66.0 g of acetone, 20.0 g of ethyl acetate, 5.0 g of butyl acetate, 1.0 g of a lanolin derivative and a proper amount of perfume were added to give a uniform solution. Then, a proper amount of propionic acid was added thereto to give a nail enamel remover.

A monitoring test was carried out as to a facility of use of the nail enamel remover by 10 women in their twenties who have ever used a conventional nail enamel remover. The results are evaluated in accordance with the following criteria for evaluation. The results are shown in Table 8.

[Criteria for evaluation]

A: The nail enamel remover scarcely dripped from nails and could be easily used.

B: No feeling was especially observed.

C: The viscosity of the nail enamel remover was too high to use.

TABLE 8

| | Facility of use of nail enamel remover (Number of persons) | | |
|---|---|---|---|
| Example No. | A | B | C |
| 28 | 7 | 2 | 1 |

In Table 8, the "B" level shows the level of conventional nail enamel remover. From the results shown in Table 8, it can be seen that the obtained nail enamel remover containing the cationic thickener scarcely drips from a nail and can be easily used.

EXAMPLE 29

To 0.3 g of the cationic thickener obtained in Preparative example 1, 4.0 g of propylene glycol, 2.0 g of polyethylene glycol 1500, 2.0 g of polyoxyethylene (25) oleyl ether, 15.0 g of ethyl alcohol, 76.7 g of purified water and a proper amount of perfume were added and its pH was adjusted to 5.5 by using lactic acid to obtain lotion.

A monitoring test was carried out as to feeling when the obtained lotion was used by 10 women in their twenties who have ever used conventional lotion. The results are evaluated in accordance with the following criteria for evaluation. The results are shown in Table 9.

[Criteria for evaluation]

A: No stickiness was imparted and wet feeling was maintained.

B: Smooth feeling and no stickiness were imparted.

C: No feeling was especially observed.

D: The skin was sticky.

TABLE 9

| | Feeling when lotion was used (Number of persons) | | | |
|---|---|---|---|---|
| Example No. | A | B | C | D |
| 29 | 4 | 5 | 1 | 0 |

In Table 9, the "C" level shows the level of conventional lotion. From the results shown in Table 9, it can be seen that the obtained lotion containing the cationic thickener does not show stickiness and imparts wet and excellent feeling to skin.

EXAMPLE 30

| | (Parts by weight) |
|---|---|
| (1) Vaselin | 4.3 |
| (2) Dimethylpolysiloxane (5cSt/25° C.) | 3.1 |
| (3) Glyceryl tri-2-ethylhexanoate | 3.1 |
| (4) Liquid paraffin | 10.9 |
| (5) Potassium stearate | 2.1 |
| (6) POE(20) cetyl ether | 2.1 |
| (7) Glycerin | 10.1 |
| (8) 1,3-Butylene glycol | 5.1 |
| (9) Purified water | 55.6 |
| (10) Cationic thickener obtained in Preparative Example 1 | 3.0 |
| (11) Lactic acid | 0.6 |
| (12) Paraben | Proper amount |
| (13) Perfume | Proper amount |

The components (1), (2), (3), (4) and (13) were heated to 70° C. and dissolved to obtain an oily component. On the other hand, the components (5), (6), (7), (8), (9), (10), (11) and (12) were stirred, dissolved and heated to 70° C. to obtain an aqueous component. The oily component was gradually added to the aqueous component, and they were emulsified with an emulsifier. After that, the obtained emulsion was cooled to 30° C. by using a refrigerator to give cream.

A monitoring test was carried out as to feeling when the obtained cream was used by 20 women in their twenties who have ever used conventional cream. the results are evaluated in accordance with following criteria for evaluation. The results are shown in Table 10.

[Criteria for evaluation]

A: The cream could be widely spreaded and excellent refreshing feeling were imparted.

B: Refreshing feeling and a little stickiness were imparted.

C: No feeling was especially observed.

D: Stickiness was great and feeling was bad.

TABLE 10

| Example No. | Feeling when cream was used (Number of persons) | | | |
|---|---|---|---|---|
| | A | B | C | D |
| 30 | 12 | 6 | 2 | 0 |

In Table 10, the "C" level shows the level of conventional cream. From the results shown in Table 10, it can be seen that the obtained cream containing the cationic thickener imparts excellent refreshing feeling to users.

EXAMPLE 31

| | (Parts by weight) |
|---|---|
| (1) Stearic acid | 2.0 |
| (2) Cetyl alcohol | 0.4 |
| (3) Liquid paraffin | 25.3 |
| (4) POE(10) oleate | 1.0 |
| (5) Sorbitan trioleate | 1.0 |
| (6) Dipropylene glycol | 5.0 |
| (7) Polyethylene glycol 1500 | 5.0 |
| (8) Triethanolamine | 1.0 |
| (9) Cationic thickener obtained in Preparative Example 1 | 1.0 |
| (10) Lactic acid | 0.2 |
| (11) Purified water | 58.1 |
| (12) Paraben | Proper amount |
| (13) Perfume | Proper amount |

The components (1), (2), (3), (5) and (13) were stirred and dissolved together at 70° C. to obtain an oily component. On the other hand, the components (4), (6), (7), (8), (9), (10), (11) and (12) were stirred and dissolved together to obtain an aqueous component. The oily component was added to the aqueous component and they were emulsifier by using a emulsifier at 70° C. After that, the obtained emulsion was cooled to 30° C. to give a milky lotion.

A monitoring test was carried out as to feeling when the obtained milky lotion was used by 20 women in their twenties who have ever used a conventional milky lotion. The results are evaluated in accordance with the following criteria for evaluation. The results are shown in Table 11.
[Criteria for evaluation]
A: Excellent refreshing feeling and no stickiness were imparted.
B: Excellent refreshing feeling and a little stickiness were imparted.
C: No feeling was especially observed.
D: Stickiness was great and feeling was bad.

TABLE 11

| Example No. | Feeling when milky lotion was used (Number of persons) | | | |
|---|---|---|---|---|
| | A | B | C | D |
| 31 | 10 | 6 | 4 | 0 |

In Table 11, the "C" level shows the level of conventional milky lotion. From the results shown in Table 11, it can be seen that the obtained milky lotion containing the cationic thickener imparts excellent refreshing feeling to users.

EXAMPLE 32

| | (Parts by weight) |
|---|---|
| (1) Methylphenyl polysiloxane (20cSt/ 25° C.) | 3.0 |
| (2) Liquid paraffin | 5.0 |
| (3) Cetyl 2-ethylhexanoate | 5.0 |
| (4) Light liquid paraffin | 5.0 |
| (5) Decamethylcyclopentasiloxane | 10.0 |
| (6) Trimethylsiloxysilicic acid | 5.0 |
| (7) Octyl p-methoxycinnamate | 5.0 |
| (8) 4-Methoxy-4'-t-butyldibenzoylmethane | 1.0 |
| (9) Cationic thickener obtained in Preparative Example 3 | 2.0 |
| (10) Lactic acid | 0.4 |
| (11) Glycerin | 5.0 |
| (12) 1,3-Butylene glycol | 4.0 |
| (13) Sodium stearate | 5.0 |
| (14) Glycerol monostearate | 2.0 |
| (15) Purified water | 42.6 |
| (16) Paraben | Proper amount |
| (17) Disodium edetate | Proper amount |
| (18) Perfume | Proper amount |

The components (1), (2), (3), (4), (5), (6), (7), (8) and (18) were heated to 70° C. and dissolved together to give an oily component. On the other hand, the components (9), (10), (11), (12), (13), (14), (15), (16) and (17) were stirred and dissolved together, and heated to 70° C. to give an aqueous component. The oily component was gradually added to the aqueous component and they were emulsified by using a emulsifier. After that, the obtained emulsion was cooled to 30° C. by using a refrigerator to give a sun screening lotion.

A monitoring test was carried out as to feeling when the obtained sun screening lotion was used by 10 men in their twenties and 10 women in their twenties who have ever used conventional sun screening lotion. The results are evaluated in accordance with the following criteria for evaluation. The results are shown in Table 12.
[Criteria for evaluation]
A: Excellent refreshing feeling and no stickiness were imparted.
B: Excellent refreshing feeling and a little stickiness were imparted.
C: No feeling was especially observed.
D: Stickiness was great and feeling was bad.

TABLE 12

| Example No. | Feeling when the sun screening lotion was used (Number of persons) | | | |
|---|---|---|---|---|
| | A | B | C | D |
| 32 | 10 | 8 | 2 | 0 |

In Table 12, the "C" level shows the level of conventional sun screening lotion. From the results shown in Table 12, it can be seen that the obtained sun screening lotion containing the cationic thickener imparts excellent refreshing feeling to users.

EXAMPLE 33

|  | (Parts by weight) |
|---|---|
| Powder | |
| (1) Talc | 3.0 |
| (2) Titanium dioxide | 5.0 |
| (3) Red iron oxide | 0.5 |
| (4) Yellow iron oxide | 1.4 |
| (5) Black iron oxide | 0.1 |
| Water phase | |
| (6) Cationic thickener obtained in Preparative Example 1 | 0.8 |
| (7) Lactic acid | 0.4 |
| (8) Polyoxyethylene sorbitan monostearate | 0.9 |
| (9) Triethanolamine | 1.0 |
| (10) Propylene glycol | 10.0 |
| (11) Purified water | 55.7 |
| Oil phase | |
| (12) Stearic acid | 2.2 |
| (13) Isohexadecyl alcohol | 7.0 |
| (14) Glycerol monostearate | 2.0 |
| (15) Liquid lanoline | 2.0 |
| (16) Liquid paraffin | 8.0 |
| (17) Paraben | Proper amount |
| (18) Perfume | Proper amount |

The components (10), (6) and (7) were added to the component (11) and they were blended. After the mixture was mixed at 70° C. by using a homomixer, the components (8) and (9) were added thereto and sufficiently stirred. The components (1), (2), (3), (4) and (5) which were previously sufficiently mixed and pulverized was added thereto with stirring, and then the mixture was heated to 70° C. by using a homomixer. To the mixture, the components (12), (13), (14), (15), (16) and (17) which were previously heated to 70° to 80° C. was gradually added, and they were mixed together at 70° C. by using a homomixer. After the obtained mixture was cooled with stirring and the component (18) was added thereto at 45° C., they were cooled to room temperature.

Finally, degassing was carried out to give an emulsified foundation.

A monitoring test was carried out as to feeling when the obtained emulsified foundation was used by 20 women in their twenties who have ever used conventional emulsified foundation. The results are evaluated in accordance with the following criteria for evaluation. The results are shown in Table 13.

[Criteria for evaluation]

A: The emulsified foundation could be widely spreaded and excellent refreshing feeling and no stickiness were imparted.

B: Excellent refreshing feeling and a little stickiness were imparted.

C: No feeling was especially observed.

D: Stickiness was great and feeling was bad.

TABLE 13

| Example No. | Feeling when emulsified foundation was used (Number of persons) | | | |
|---|---|---|---|---|
| | A | B | C | D |
| 33 | 8 | 10 | 2 | 0 |

In Table 13, the "C" level shows the level of conventional emulsified foundation. From the results shown in Table 13, it can be seen that the obtained emulsified foundation containing the cationic thickener imparts excellent refreshing feeling to users.

EXAMPLE 34

|  | (Parts by weight) |
|---|---|
| (1) 1,3-Butylene glycol | 3.0 |
| (2) Dipropylene glycol | 3.0 |
| (3) Glycerol | 3.0 |
| (4) Paraben | 0.2 |
| (5) Purified water | 38.9 |
| (6) Polyoxyethylene (10) sorbitan monooleate | 0.5 |
| (7) Black iron oxide | 8.0 |
| (8) Kaolin | 10.0 |
| (9) Cationic thickener obtained in Preparative Example 2 | 2.0 |
| (10) Lactic acid | 0.4 |
| (11) Squalane | 1.0 |
| (12) Emulsion of butyl acrylate-methyl methacrylate copolymer | 30.0 |

The components (1), (2), (3), (4), (5), (6), and (10) were dissolved together. The components (11) and (12) were added thereto and mixed with stirring. The components (7) and (8) were added thereto and mixed to give an eyeliner.

A monitoring test was carried out as to feeling when the obtained eyeliner was used by 20 women in their twenties who have ever used conventional eyeliner. The results are evaluated in accordance with the following criteria for evaluation. The results are shown in Table 14.

[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 14

| Example No. | Feeling when eyeliner was used (Number of persons) | | | |
|---|---|---|---|---|
| | A | B | C | D |
| 34 | 12 | 6 | 2 | 0 |

In Table 14, the "C" level shows the level of conventional eyeliner. From the results shown in Table 14, it can be seen that the obtained eyeliner containing the cationic thickener imparts excellent refreshing feeling to users.

EXAMPLE 35

|     | (Parts by weight) |
| --- | --- |
| (1) Cetyltrimethylammonium chloride | 0.6 |
| (2) Cetearyl alcohol | 4.0 |
| (3) Squalane | 3.0 |
| (4) Glycerol monostearate | 1.0 |
| (5) Stearic acid | 0.5 |
| (6) Cationic thickener obtained in Preparative Example 1 | 5.0 |
| (7) Lactic acid | 1.4 |
| (8) EDTA-3Na | Proper amount |
| (9) Purified water | 84.5 |
| (10) Perfume | Proper amount |

The components (2), (3), (4), (5) and (10) were heated to 70° C. and dissolved together to obtain an oily component. On the other hand, the components (6), (7), (8) and (9) were stirred and dissolved together, and heated to 70° C. to obtain an aqueous component. After the oily component was gradually added to the aqueous component and they are emulsified with an emulsifier. Then, the obtained emulsion was cooled to 30° C. to give a hair rinse.

A monitoring test was carried out as to feeling when the obtained hair rinse was used by 10 men in their twenties and 10 women in their twenties who have ever used conventional hair rinse. The results are evaluated in accordance with the following criteria for evaluation. The results are shown in Table 15.

[Criteria for evaluation]

A: No stickiness was imparted and hair had smoothness.

B: A little stickiness was imparted and hair had a little smoothness.

C: No feeling was especially observed.

D: Stickiness was great and feeling was bad.

TABLE 15

| | Feeling when hair rinse was used (Number of persons) | | | |
| --- | --- | --- | --- | --- |
| Example No. | A | B | C | D |
| 35 | 11 | 7 | 2 | 0 |

In Table 15, the "C" level shows the level of conventional hair rinse. From the results shown in Table 15, it can be seen that the obtained hair rinse containing the cationic thickener shows a little stickiness and imparts smoothness to hair.

EXAMPLE 36

|     | (Parts by weight) |
| --- | --- |
| (1) Triethanolamine lauryl sulfate (40% aqueous solution) | 30.0 |
| (2) Sodium polyoxyethylene (3) lauryl ether sulfate (30% aqueous solution) | 20.0 |
| (3) Lauryldiethanolamide | 5.0 |
| (4) Glycerol monopalmitic acid ester | 1.0 |
| (5) Lanolin derivative | 2.0 |
| (6) Propylene glycol | 5.0 |
| (7) Cationic thickener obtained in Preparative Example 1 | 1.0 |
| (8) Phosphoric acid | 0.5 |
| (9) Purified water | 35.5 |
| (10) Perfume | Proper amount |
| (11) Paraben | Proper amount |
| (12) EDTA-3Na | Proper amount |

The components (1), (2), (3), (4), (5), (6), (7), (10) and (11) were added to the components (9) and they were stirred. Then, the obtained mixture was heated to 70° C. and uniformly dissolved together. After that, the component (8) was added thereto and stirred and dissolved therein to give a face cleansing gel.

A monitoring test was carried out as to feeling when the obtained face cleansing gel was used by 20 women in their twenties who have ever used conventional face cleansing gel. The results are evaluated in accordance with the following criteria for evaluation. The results are shown in Table 16.

[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 16

| | Feeling when face cleansing gel was used (Number of persons) | | | |
| --- | --- | --- | --- | --- |
| Example No. | A | B | C | D |
| 36 | 8 | 8 | 4 | 0 |

In Table 16, the "C" level shows the level of conventional face cleansing gel. From the results shown in Table 16, it can be seen that the obtained face cleansing gel containing the cationic thickener imparts excellent refreshing feeling to users.

EXAMPLE 37

|     | (Parts by weight) |
| --- | --- |
| (1) Squalane | 20.0 |
| (2) Cetyl isooctanoate | 8.5 |
| (3) Microcrystalline wax | 1.0 |
| (4) Organic modified bentonite | 1.3 |
| (5) Polyoxyethylene glycerol triisostearate | 1.0 |
| (6) Glycerol | 10.0 |
| (7) Cationic thickener obtained in Preparative Example 1 | 1.0 |
| (8) Lactic acid | 0.3 |
| (9) Antiseptic | Proper amount |
| (10) Perfume | Proper amount |
| (11) Purified water | 56.9 |

The components (1), (2) and (3) were heated to melt and the components (4), (5), (9) and (10) were added thereto. After the temperature of the mixture was adjusted to 70° C., the mixture was uniformly dispersed and dissolved to obtain an oily gel. On the other hand, the components (6), (7) and (8) were added to the component (11) and the temperature of the mixture was adjusted to 70° C. to obtain an aqueous component. The aqueous component was gradually added to the oily gel with sufficiently stirring. The obtained mixture was uniformly mixed by using a homomixer. After that, degassing and filtration were carried out and the mixture was cooled to 30° C. to give eye wrinkle cream.

A monitoring test was carried out as to feeling when the obtained eye wrinkle cream was used by 20 women in their twenties who have ever used conventional eye wrinkle cream. The results are evaluated in accordance with the following criteria for evaluation. The results are shown in Table 17.

[Criteria for evaluation]

A: Excellent refreshing feeling and no stickiness were imparted.

B: Excellent refreshing feeling and a little stickiness were imparted.

C: No feeling was especislly observed.

D: Stickiness was great and feeling was bad.

TABLE 17

| | Feeling when eye wrincle cream was used (Number of persons) | | | |
|---|---|---|---|---|
| Example No. | A | B | C | D |
| 37 | 8 | 8 | 4 | 0 |

In Table 17, the "C" level shows the level of conventional eye wrincle cream. From the results shown in Table 17, it can be seen that the obtained eye wrincle cream containing the cationic thickener imparts excellent refreshing feeling to users.

EXAMPLE 38

| | (Parts by weight) |
|---|---|
| (1) Dipropylene glycol | 7.0 |
| (2) Polyethylene glycol 1500 | 8.0 |
| (3) Cationic thickener obtained in Preparative Example 1 | 0.8 |
| (4) Lactic acid | 0.5 |
| (5) Polyethylene glycol (15) oleyl alcohol ether | 1.0 |
| (6) Paraben | Proper amount |
| (7) EDTA-3Na | Proper amount |
| (8) Perfume | Proper amount |
| (9) Purified water | 82.6 |

The component (3) was uniformly dissolved in the component (9), and the components (2) and (7) were added thereto to give an aqueous component.

On the other hand, the component (5) was added to the component (1) and the mixture was heated and dissolved at a temperature of 50° to 55° C., and the components (6) and (8) were added thereto. The aqueous component was gradually added thereto with stirring. Finally, the component (4) was added to the resulting mixture and the obtained mixture was sufficiently stirred to give a moisturizing gel.

A monitoring test was carried out as to feeling when the obtained moisturizing gel was used by 20 women in their twenties who have ever used conventional moisturizing gel. The results are evaluated in accordance with the following criteria for evaluation. The results are shown in Table 18.

[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 18

| | Feeling when moisturizing gel was used (Number of persons) | | | |
|---|---|---|---|---|
| Example No. | A | B | C | D |
| 38 | 12 | 6 | 2 | 0 |

In Table 18, the "C" level shows the level of conventional moisturizing gel. From the results shown in Table 18, it can be seen that the obtained moisturizing gel containing the cationic thickener imparts excellent refreshing feeling to users.

EXAMPLE 39

| | (Parts by weight) |
|---|---|
| Oily component | |
| (1) Isostearic acid | 0.8 |
| (2) Stearic acid | 1.6 |
| (3) Diglycerol diisostearate | 2.0 |
| (4) Vaseline | 2.0 |
| (5) Squalane | 10.0 |
| (6) Cetyl 2-ethylhexanoate | 8.0 |
| (7) Potassium hydroxide | 0.27 |
| Aqueos component | |
| (8) Dipropylene glycol | 5.0 |
| (9) Concentrated glycerin | 7.0 |
| (10) Deionized water | 54.03 |
| (11) Bentonite | 0.8 |
| (12) Cationic thickener obtained in Preparative Example 1 | 1.0 |
| (13) Lactic acid | 0.5 |
| Powder | |
| (14) Talc | 7.0 |
| (15) Perfume | Proper amount |
| (16) Paraben | Proper amount |

The components (8), (9), (10) and (11) were blended and heated to 70° C. by using a homomixer. The component (14) was added thereto and the resulting mixture was again admixed by using the homomixer. Then, the component (7) was added thereto to give an aqueous component.

On the other hand, the components (1), (2), (3), (4), (5) and (6) were heated and dissolved together at a temperature of 70° to 80° C., and the components (15) and (16) were added thereto to give an oily component. The oily component was added to the aqueous component, and they were emulsified by using a homomixer. After that, degassing was carried out and the mixture was cooled to 30° C. Then, the components (12) and (13) were added to the mixture and the mixture was stirred to mix to give a base make up composition.

A monitoring test was carried out as to feeling when the obtained base make up composition was used by 20 women in their twenties who have ever used conventional base make up composition. The results are evaluates in accordance with the following criteria for evaluation. The results are shown in Table 19.

[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 19

| Example No. | Feeling when base make up composition was used (Number of persons) | | | |
|---|---|---|---|---|
| | A | B | C | D |
| 39 | 10 | 6 | 4 | 0 |

In Table 19, the "C" level shows the level of conventional base make up composition. From the results shown in Table 19, it can be seen that the obtained base make up composition containing the cationic thickener imparts excellent refreshing feeling to users.

EXAMPLE 40

| | (Parts by weight) |
|---|---|
| (1) Cationic thickener obtained in Preparative Example 1 | 3.0 |
| (2) Lactic acid | 1.72 |
| (3) Vinylpyrrolidone-vinyl acetate copolymer | 15.0 |
| (4) 1,3-Butanediol | 2.0 |
| (5) Purified water | 78.28 |
| (6) Antiseptic | proper amount |

The component (6) was dissolved in the component (4), and the component (5) was added thereto. After the component (2) was added thereto and stirred and dissolved, the component (1) was gradually added thereto and the obtained mixture was stirred and dissolved together. After that, degassing was carried out to give an aqueous mascara.

A monitoring test was carried out as to feeling when the obtained aqueous mascara was used by 20 women in their twenties who have ever used conventional mascara. The results are evaluated in accordance with the following criteria for evaluation. The results are shown in Table 20.
[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 20

| Example No. | Feeling when aqueous mascara was used (Number of persons) | | | |
|---|---|---|---|---|
| | A | B | C | D |
| 40 | 12 | 6 | 2 | 0 |

In Table 20, the "C" level shows the level of conventional mascara. From the results shown in Table 20, it can be seen that the obtained aqueous mascara containing the cationic thickener imparts excellent refreshing feeling to users.

EXAMPLE 41

| | (Parts by weight) |
|---|---|
| (1) Emulsion of polyvinyl acetate (Solid content: 50% by weight) | 8.0 |
| (2) Emulsion acrylic polymer (Solid content: 50% by weight) | 60.0 |
| (3) Deionized water | 17.0 |
| (4) Polyoxyethylene sorbitan monooleate | 1.0 |
| (5) Thickener (bentonite) | 0.5 |
| (6) Cationic thickener obtained in Preparative Example 1 | 1.0 |
| (7) Lactic acid | 0.6 |
| (8) Isopropyl alcohol | 5.0 |
| (9) Diethylene glycol monoethyl ether | 5.0 |
| (10) Pigment | 2.0 |
| (11) Paraben | Proper amount |

The components (4), (5) and (10) were added to the component (2), and the obtained mixture was sufficiently stirred by using a homogenizer to give a mixture (A). On the other hand, the component (9) was dissolved in the component (3), and the component (6) was gradually added thereto with stirring to give a mixture (B). The mixture (B) was added to the mixture (A), and the components (1), (5), (7), (8) and (11) were added thereto and stirred. After that, degassing was carried out to give an aqueous enamel.

A monitoring test was carried out as to feeling when the obtained aqueous enamel was used by 20 women in their twenties who have ever used convantional enamel. The results are evaluated in accordance with the following criteria for evaluation. The results are shown in Table 21.
[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 21

| Example No. | Feeling when aqueous enamel was used (Number of persons) | | | |
|---|---|---|---|---|
| | A | B | C | D |
| 41 | 12 | 6 | 2 | 0 |

In Table 21, the "C" level shows the level of conventional enamel. From the results shown in Table 21, it can be seen that the obtained aqueous enamel containing the cationic thickener imparts excellent refreshing feeling to users.

EXAMPLE 42

| | (Parts by weight) |
|---|---|
| (1) Ethanol (95%) | 20.0 |
| (2) Amphoteric high molecular compound (N-methacryloylethyl N,N-dimethyl-ammonium/α-N-methylcarboxyl betaine-butyl methacrylate copolymer) | 1.5 |
| (3) Polyoxyethylene (12) lauryl ether | 0.1 |
| (4) 1,3-Butylene glycol | 0.4 |
| (5) Polyoxyethylene (60) hydrogenated castor oil | 0.5 |

|  | (Parts by weight) |
|---|---|
| (6) Dimethyl polysiloxane | 2.0 |
| (7) Cationic thickener obtained in Preparative Example 1 | 1.0 |
| (8) Lactic acid | 0.5 |
| (9) Purified water | 74.0 |
| Propellant: LPG | |
| Total amount of components (1) to (9)/Propellant = 50/50 (weight ratio) | |

The component (7) was dissolved in the component (9), and a mixture of the components (4), (5) and (6) and a little amount of the component (9) was added thereto. Then, the components (1), (2) and (3) were added thereto and mixed together. After a can was charged with this mixture, the can was charged with a propellant to give a foamy aerosol cosmetic composition.

A monitoring test was carried out as to feeling when the obtained foamy aerosol cosmetic composition was used by 10 men in their twenties and 10 women in their twenties who have ever used conventional foamy aerosol cosmetic composition. The results are evaluated in accordance with the following criteria for evaluation. The results are shonw in Table 22.

[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 22

| | Feeling when foamy aerosol cosmetic composition was used (Number of persons) | | | |
|---|---|---|---|---|
| Example No. | A | B | C | D |
| 42 | 14 | 4 | 2 | 0 |

In Table 22, the "C" level shows the level of conventional foamy aerosol cosmetic composition. From the results shown in Table 22, it can be seen that the obtained foamy aerosol cosmetic composition containing the cationic thickener imparts excellent refreshing feeling to users.

EXAMPLE 43

|  | (Parts by weight) |
|---|---|
| (1) Ethanol (95%) | 15.0 |
| (2) Amphoteric high molecular compound (N-methacryloylethyl N,N-dimethyl-ammonium α-N-methylcarboxyl betaine-butyl methacrylate copolymer) | 0.5 |
| (3) Aminomethylpropanol | 0.1 |
| (4) Polyoxyethylene (20) octyl ether | 0.5 |
| (5) Liquid paraffin | 5.0 |
| (6) Glycerol | 3.0 |
| (7) Perfume | Proper amount |
| (8) Methyl paraben | Proper amount |
| (9) Cationic thickener obtained in Preparative Example 1 | 0.7 |
| (10) Lactic acid | 0.4 |
| (11) Purified water | 74.8 |

|  | (Parts by weight) |
|---|---|
| Propellant: LPG/DME = 70/30 (weight ratio) | |
| Total amount of the components (1) to (11)/Propellant = 80/20 (weight ratio) | |

The component (9) was dissolved in the component (11), and the components (1), (2), (3), (4), (5), (6), (7), (8) and (10) were added thereto and mixed together with stirring. After a can was charged with the obtained mixture, the can was charged with a propellant to give a later-foamable foamy aerosol cosmetic composition.

A monitoring test was carried out as to feeling when the obtained later-foamable foamy aerosol cosmetic composition was used by 10 men in their twenties and 10 women in their twenties who have ever used conventional later-foamable foamy aerosol cosmetic composition. The results are evaluated in accordance with the following criteria for evaluation. The results are shown in Table 23.

[Criteria for evaluation]

A: Excellent refreshing feeling and no stickiness were imparted.

B: Excellent refreshing feeling and a little stickiness were imparted.

C: No feeling was especially observed.

D: Stickiness was great and feeling was bad.

TABLE 23

| | Feeling when later-foamable foamy aerosol cosmetic composition was used (Number of persons) | | | |
|---|---|---|---|---|
| Example No. | A | B | C | D |
| 43 | 12 | 6 | 2 | 0 |

In Table 23, the "C" level shows the level conventional later-foamable foamy aerosol cosmetic composition. From the results shown in Table 23, it can be seen that the obtained later-foamable foamy aerosol cosmetic composition containing the cationic thickener imparts excellent refreshing feeling to users.

EXAMPLE 44

|  | (Parts by weight) |
|---|---|
| (1) Brack (No. 401) | 0.2 |
| (2) Purple (No. 401) | 0.3 |
| (3) Yellow (No. 4) | 0.1 |
| (4) Benzyl alcohol | 5.0 |
| (5) Cationic thickener obtained in Preparative Example 1 | 1.0 |
| (6) Citric acid | 0.5 |
| (7) EDTA-3Na | Proper amount |
| (8) Purified water | 91.4 |

The component (4) was added to the component (8), and the components (5), (6) and (7) were gradually added thereto to give a viscous solution. To the viscous solution, the components (1), (2) and (3) were added and the obtained mixture was uniformly stirred and mixed together to give an acidic hair dye.

A monitoring test was carried out as to feeling when the obtained acidic hair dye was used by 20 men in their twenties who have ever used conventional acidic hair dye.

The results are evaluated in accordance with the following criteria for evaluation. The results are shown in Table 24.

[Criteria for evaluation]

A: No stickiness was imparted, and hair had smoothness.
B: A little stickiness was imparted and hair had a little smoothness.
C: No feeling was especially observed.
D: Stickiness was great and feeling was bad.

TABLE 24

| Example No. | Feeling when acidic hair dye was used (number of persons) | | | |
|---|---|---|---|---|
| | A | B | C | D |
| 44 | 10 | 8 | 2 | 0 |

In Table 24, the "C" level shows the level of conventional hair dye for the hair. From the results shown in Table 24, it can be seen that the obtained acidic hair dye containing the cationic thickener shows no stickiness and imparts excellent feeling to users.

EXAMPLE 45

| [First agent] | (Parts by weight) |
|---|---|
| (1) p-Phenylenediamine | 3.0 |
| (2) Resorcin | 0.5 |
| (3) Oleic acid | 20.0 |
| (4) Polyoxyethylene (10) oleyl alcohol ether | 15.0 |
| (5) Isopropyl alcohol | 10.0 |
| (6) Aqueous ammonia (28%) | 10.0 |
| (7) Cationic thickener obtained in Preparative Example 1 | 1.0 |
| (8) Purified water | 40.5 |
| (9) Butylhydroxytoluene | Proper amount |
| (10) EDTA-3Na | Proper amount |

The components (3), (4), (5), (6), (7), (8), (9) and (10) are uniformly mixed together with stirring and the components (1) and (2) were added thereto to give a first agent for hair dye.

| [Second agent] | (Parts by weight) |
|---|---|
| (1) Hydrogen peroxide aqueous solution (30%) | 20.0 |
| (2) Purified water | 79.3 |
| (3) Stabilizer | Proper amount |
| (4) Phosphoric acid | 0.3 |

The components (1), (2), (3) and (4) were mixed to give a second agent for hair dye.

A hair dye was prepared by mixing the first agent and the second agent when the hair dye was used, which was viscous.

A monitoring test was carried out as to feeling when the obtained hair dye was used by 20 men in their twenties who have ever used conventional hair dye. The results are evaluated in accordance with the following criteria for evaluation. The results are shown in Table 25.

[Criteria for evaluation]

A: No stickiness was imparted and there was adhesiveness to hair.
B: A little stickiness was imparted and there was a little adhesiveness to hair.
C: No feeling was especially observed.
D: Stickiness was great and feeling was bad.

TABLE 25

| Example No. | Feeling when hair dye was used (Number of persons) | | | |
|---|---|---|---|---|
| | A | B | C | D |
| 45 | 12 | 4 | 4 | 0 |

In Table 25, the "C" level shows the level of conventional hair dye. From the results shown in Table 25, it can be seen that the obtained hair dye containing the cationic thickener shows no stickiness and excellent adhesiveness to hair and imparts excellent feeling to users.

EXAMPLE 46

| | (Parts by weight) |
|---|---|
| (1) Sodium laurylpolyoxyethylene (3) sulfate | 9.0 |
| (2) Sodium lauryl sulfate | 4.0 |
| (3) Coconut oil fatty acid diethanolamide | 4.0 |
| (4) Glycerol | 1.0 |
| (5) Cationic thickener obtained in Preparative Example 1 | 0.2 |
| (6) Lactic acid | 0.5 |
| (7) Perfume | Proper amount |
| (8) Colorant | Proper amount |
| (9) EDTA-3Na | Proper amount |
| (10) Purified water | 81.3 |

The components (5), (6), (7), (8) and (9) were gradually added to the component (10), and mixing them with stirring, and the obtained mixture was heated to 70° C. After the components (1), (2), (3) and (4) were added thereto and mixed with stirring, the obtained mixture was cooled to 30° C. to give a one step shampoo.

A moniroting test was carried out as to feeling when the obtained one step shampoo was used by 20 women in their twenties who have ever used conventional one step shampoo. The results are evaluated in accordance with the following criteria for evaluation. The results are shown in Table 26.

[Criteria for evaluation]

A: No stickiness was imparted and hair had smoothness.
B: A little stickiness was imparted and hair had a little smoothness.
C: No feeling was especially observed.
D: Stickiness was great and feeling was bad.

TABLE 26

| Example No. | Feeling when one step shampoo was used (Number of persons) | | | |
|---|---|---|---|---|
| | A | B | C | D |
| 46 | 12 | 6 | 2 | 0 |

In Table 26, the "C" level shows the level of conventional one step shampoo. From the results shown in Table 26, it can be seen that the obtained one step shampoo containing the cationic thickener shows no stickiness and imparts excellent feeling to users and smoothness can be imparted to hair.

EXAMPLE 47

|  | (Parts by weight) |
|---|---|
| (1) Coconut oil | 10.0 |
| (2) Tallow | 5.0 |
| (3) Lauric acid | 5.0 |
| (4) Myristic acid | 4.0 |
| (5) Methylpolysiloxane | 0.5 |
| (6) Propylene glycol | 10.0 |
| (7) 1,3-Butylene glycol | 5.0 |
| (8) di-α-Tocopheryl acetate | 0.05 |
| (9) Potassium hydroxide | 5.0 |
| (10) Methyl cellulose | 0.5 |
| (11) EDTA-3Na | 0.1 |
| (12) Cationic thickener obtained in Preparative Example 1 | 0.5 |
| (13) Phosphoric acid | 0.3 |
| (14) Perfume | Proper amount |
| (15) Purified water | 54.35 |

The components (1), (2), (3), (4), (5), (6), (7) and (8) were heated to melt, and the component (9) was added thereto. After that, the components (10), (11), (12), (13) and (14) were dissolved in the component (15), and they were added to the above mixture and mixed with stirring to give a body shampoo.

A monitoring test was carried out as to feeling when the obtained body shampoo was used by 20 women in their twenties who have ever used conventional body shampoo. The results are evaluated in accordance with the following criteria for evaluation. The results are shown in Table 27.

[Criteria for evaluation]

A: No stickiness was imparted and skin had smoothness.

B: A little stickiness was imparted and skin had a little smoothness.

C: No feeling was especially observed.

D: Stickiness was great and feeling was bad.

TABLE 27

| Example No. | Feeling when body shampoo was used (Number of persons) | | | |
|---|---|---|---|---|
|  | A | B | C | D |
| 47 | 11 | 6 | 3 | 0 |

In Table 27, the "C" level shows the level of conventional body shampoo. From the results shown in Table 27, it can be seen that the obtained body shampoo containing the cationic thickener shows no stickiness and imparts excellent feeling to users and smoothness can be imparted to skin.

EXAMPLE 48

|  | (Parts by weight) |
|---|---|
| (1) 1,3-Butylene glycol | 15.0 |
| (2) Polyoxypropylene (9) diglyceryl ether | 15.0 |
| (3) Dipropylene glycol | 10.0 |
| (4) Carboxyvinyl polymer | 0.5 |
| (5) Xanthan gum | 0.5 |
| (6) Methyl p-hydroxybenzoate | 0.1 |
| (7) Methylpolysiloxane | 5.0 |
| (8) Perfume | Proper amount |
| (9) Cationic thickener obtained in Preparative Example 1 | 0.6 |
| (10) Lactic acid | 0.3 |
| (11) Purified water | 53.0 |

The components (1), (2), (3), (4), (5) and (6) were dissolved in the component (11), and the components (7) and (8) were mixed therewith and stirred. After that, the components (9) and (10) were added thereto to give a body rinse.

A monitoring test was carried out as to feeling when the obtained body rinse was used by 20 women in their twenties who have ever used conventional body rinse. The results are evaluated in accordance with the following criteria for evaluation. The results are shown in Table 28.

[Criteria for evaluation]

A: No stickiness was imparted and skin had smoothness.

B: A little stickiness was imparted and skin had a little smoothness.

C: No feeling was especially observed.

D: Stickiness was great and feeling was bad.

TABLE 28

| Example No. | Feeling when body rinse was used (Number of persons) | | | |
|---|---|---|---|---|
|  | A | B | C | D |
| 48 | 12 | 6 | 2 | 0 |

In Table 28, the "C" level shows the level of conventional body rinse. From the results shown in Table 28, it can be seen that the obtained body rinse containing the cationic thickener shows no stickiness and imparts excellent feeling to users and smoothness can be imparted to skin.

EXAMPLE 49

|  | (Parts by weight) |
|---|---|
| (1) Concentrated glycerol | 5.0 |
| (2) 1,3-Butylene glycol | 5.0 |
| (3) Propylene glycol | 3.0 |
| (4) Methyl p-hydroxybenzonate | 0.1 |
| (5) Carboxyvinyl polymer | 0.3 |
| (6) Polyoxyethylene (60) hydrogenated castor oil | 1.0 |
| (7) Squalane | 3.0 |
| (8) Glycerol trioctanoic acid ester | 2.0 |
| (9) di-α-Tocopheryl acetate | 0.05 |
| (10) Perfume | Proper amount |
| (11) Cationic thickener obtained in Preparative Example 1 | 0.6 |
| (12) Lactic acid | 0.3 |
| (13) Purified water | 79.65 |

The components (1), (2), (3), (4) and (5) were dissolved in the component (13), and the components (6), (7), (8), (9) and (10) which were previously heated to melt were mixed therewith and stirred. After that, the components (11) and (12) were added thereto and mixed with stirring to give a body massaging gel.

A monitoring test was carried out as to feeling when the obtained body massaging gel was used by 20 women in their twenties who have ever used conventional body massaging gel. The results are evaluated in accordance with the following criteria for evaluation. The results are shown in Table 29.

[Criteria for evaluation]

A: Excellent refreshing feeling and no stickiness were imparted.

B: Excellent refreshing feeling and a little stickines were imparted.

C: No feeling was especially observed.

D: Stickiness was great and feeling was bad.

TABLE 29

| Example No. | Feeling when body massaging gel was used (Number of persons) | | | |
|---|---|---|---|---|
| | A | B | C | D |
| 49 | 14 | 5 | 1 | 0 |

In Table 29, the "C" level shows the level of conventional body massaging gel. From the results shown in Table 29, it can be seen that the obtained body massaging gel containing the cationic thickener shows no stickiness and imparts excellent feeling to users and smoothness can be imparted to skin.

EXAMPLE 50

| | (Parts by weight) |
|---|---|
| (1) Purified water | 81.1 |
| (2) Ethanol | 10.0 |
| (3) Nonionic polymer for setting (PVA6450 commercially available from Osaka Yuki Yagaku Kogyo Kabushiki Kaisha) | 1.0 |
| (4) Cationic polymer for setting (HCP-3A commercially available from Osaka Yuki Yagaku Kogyo Kabushiki Kaisha) | 2.0 |
| (5) Propylene glycol | 5.0 |
| (6) Lactic acid | 0.2 |
| (7) UV-absorber | Proper amount |
| (8) Perfume | Proper amount |
| (9) Cationic thickener obtained in Preparative Example 1 | 0.7 |

The components (2), (3), (4), (5), (6) and (7) were mixed with the component (1) with stirring, and the component (8) was added thereto. The obtained mixture was stirred and dissolved together. Then, the component (9) was added thereto and the obtained mixture was stirred and dissolved to give a viscous liquid hair dressing agent. The viscosity of the viscous liquid hair dressing agent was measured by using a B,H type Brookfield viscometer. As a result, the viscosity was 15,000 cP at 25° C.

A monitoring test was carried out as to feeling when the obtained viscous liquid hair dressing agent was used by 10 men in their twenties and 10 women in their twenties who have ever used conventional jellified hair dressing agent. The results are evaluated in accordance with the following criteria for evaluation. The results are shown in Table 30.

[Criteria for evaluation]

A: No stickiness and smooth feeling were imparted.

B: A little stickiness and a little smooth feeling were imparted.

C: No feeling was especially observed.

D: Stickiness was great and feeling was bad.

TABLE 30

| Example No. | Feeling when viscous liquid hair dressing agent was used (Number of persons) | | | |
|---|---|---|---|---|
| | A | B | C | D |
| 50 | 14 | 5 | 1 | 0 |

In Table 30, the "C" level shows the level of conventional jellified hair dressing agent. From the results shown in Table 30, it can be seen that the obtained viscous liquid hair dressing agent containing the cationic thickener shows no stickiness and imparts excellent feeling to users.

EXAMPLE 51

| | (Parts by weight) |
|---|---|
| (1) Purified water | 42.4 |
| (2) Glycerol | 10.0 |
| (3) Sodium L-glutamate | 2.0 |
| (4) Sodium hyaluronate | 0.1 |
| (5) Cationic thickener obtained in Preparative Example 3 | 0.5 |
| (6) Lactic acid | 0.3 |
| (7) Antiseptic | 0.3 |
| (8) Glycerol triisooctanoate | 5.0 |
| (9) Decamethylcyclopentasiloxane | 10.0 |
| (10) Dimethylpolysiloxane (6cSt/25° C.) | 5.0 |
| (11) Dimethylpolysiloxane-methyl(polyoxyethylene)polysiloxane copolymer (Content of polyoxyethylene: 20% by weight) | 4.0 |
| (12) Antioxidant | 0.1 |
| (13) Perfume | 0.3 |
| (14) Sericite treated with silicone | 7.4 |
| (15) Talc treated with silicone | 1.0 |
| (16) Zinc oxide treated with silicone | 2.0 |
| (17) Titanium oxide treated with silicone | 8.0 |
| (18) Yellow iron oxide treated with silicone | 1.0 |
| (19) Red iron oxide treated with silicone | 0.4 |
| (20) Black iron oxide treated with silicone | 0.2 |

The components (1), (2), (3), (4), (5), (6) and (7) were stirred and dissolved together to obtain an aqueous component. The components (8), (9), (10), (11), (12) and (13) were stirred and dissolved to obtain an oily component. The components (14), (15), (16), (17), (18), (19), and (20) were mixed with stirring to obtain powder. The aqueous component was added to the oily component at 70° C. and the obtained mixture was emulsified by using an emulsifying appratus. After that, the powder was added thereto and the obtained mixture was sufficiently mixed to obtain an emulsified foundation.

A monitoring test was carried out as to feeling when obtained emulsified foundation was used by 20 women in their twenties who have ever used conventional emulsified foundation. The results are evaluated in accordance with the following criteria for evaluation. The results are shown in Table 31.

[Criteria for evaluation]

A: No stickiness and smooth feeling were imparted.

B: A little stickiness and a little smooth feeling were imparted.

C: No feeling was especially observed.

D: Stickiness was great and feeling was bad.

TABLE 31

| Example No. | Feeling when emulsified foundation was used (Number of persons) | | | |
|---|---|---|---|---|
| | A | B | C | D |
| 51 | 10 | 8 | 2 | 0 |

In Table 31, the "C" level shows the level of conventional emulsified foundation. From the results shown in Table 31, it can be seen that the obtained emulsified foundation containing the cationic thickener shows no stickiness and imparts excellent feeling to users.

The cosmetic composition containing the cationic thickener of the present invention is not sticky and from which refreshing and excellent feeling are imparted in comparison with cosmetic compositions. Moreover, since the cosmetic composition containing the cationic thickener of the present invention has an excellent characteristic in viscosity within the almost same pH range as human skin, that is, b 4.5to 6.5, the skin is little irritated.

Also, it is expected that various new functions can be imparted to the cosmetic composition of the present invention since various new materials for cosmetics in which viscosity cannot be easily increased such as the cationic resin for setting and the cationic thickener having a high adaptability to the raw materials for cosmetics can be admixed at the same time.

In addition to the ingredients used in the Examples, other ingredients can be used in the Examples as set forth in the specification to obtain substantially the same results.

What is claimed is:

1. A cosmetic composition comprising a cationic thickener having a viscosity of 500 to 30000 cP at 20° C. when the viscosity is measured by using a BH-type Brookfield viscometer at 20 rpm after the cationic thickener is dispersed into water so that the concentration of the cationic thickener is 1% by weight, said cationic thickener prepared in a nonaqueous solvent system in the absence of water and a surface active agent by polymerizing a monomer composition containing:

(A) 15 to 90% by weight of at least one of an acrylic monomer having an amino group and a methacrylic monomer having an amino group, represented by the general formula (I):

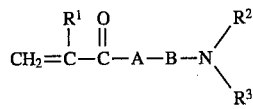

(I)

wherein $R^1$ is a hydrogen atom or methyl group, each of $R^2$ and $R^3$ is independently a hydrogen atom, methyl group, ethyl group or t-butyl group, A is oxygen atom or —NH— group, and B is a linear or branched alkylene group having 1 to 4 carbon atoms, (B) 5 to 80% by weight of N-vinylpyrrolidone, (C) 2 to 60% by weight of a monomer having at least one of acryloyl group and methacryloyl group represented by the general formula (III):

(III)

wherein $R^1$ and A are as defined above, $R^5$ is a linear or branched alkylene group having 8 to 20 carbon atoms, or a group represented by the general formula (IV):

(IV)

wherein n is an integer of 1 to 4, q is an integer of 1 to 25 and $R^6$ is a hydrogen atom or methyl group, and (D) 0.1 to 25% by weight of a crosslinkable vinyl monomer having at least two carbon-carbon unsaturated bonds.

2. The cosmetic composition of claim 1, wherein said crosslinkable vinyl monomer is a (meth)acrylic monomer having at least 2 carbon-carbon unsaturated double bonds.

3. The cosmetic composition of claim 1, wherein said monomer (C) includes a member selected from the group consisting of stearyl acryloyl and methoxy polyethyleneglycol methacryloyl.

* * * * *